United States Patent
Singh et al.

(10) Patent No.: US 10,416,740 B2
(45) Date of Patent: Sep. 17, 2019

(54) UPSAMPLING SENSORS TO AUTO-DETECT A FITNESS ACTIVITY

(71) Applicant: Google Inc., Mountain View, CA (US)

(72) Inventors: Satinder Pal Singh, Santa Clara, CA (US); Gustavo Mendes Estephanio de Moura, Mountain View, CA (US); Ke Xiao, Mountain View, CA (US)

(73) Assignee: Google LLC, Mountain View, CA (US)

( * ) Notice: Subject to any disclaimer, the term of this patent is extended or adjusted under 35 U.S.C. 154(b) by 531 days.

(21) Appl. No.: 14/836,628

(22) Filed: Aug. 26, 2015

(65) Prior Publication Data

US 2017/0056722 A1    Mar. 2, 2017

(51) Int. Cl.
| | |
|---|---|
| *A61B 5/00* | (2006.01) |
| *G06F 1/3234* | (2019.01) |
| *A61B 5/11* | (2006.01) |
| *G06F 1/26* | (2006.01) |
| *G06F 1/16* | (2006.01) |
| *G06F 19/00* | (2018.01) |

(Continued)

(52) U.S. Cl.
CPC .............. *G06F 1/26* (2013.01); *A61B 5/1118* (2013.01); *A61B 5/1123* (2013.01); *G06F 1/163* (2013.01); *G06F 1/325* (2013.01); *G06F 19/3481* (2013.01); *A61B 5/02438* (2013.01); *A61B 5/1112* (2013.01); *A61B 5/14532* (2013.01); *A61B 5/681* (2013.01); *A61B 5/7264* (2013.01); *A61B 2560/0242* (2013.01); *A61B 2562/0219* (2013.01)

(58) Field of Classification Search
None
See application file for complete search history.

(56) References Cited

U.S. PATENT DOCUMENTS

2006/0020177 A1    1/2006 Seo et al.
2009/0319221 A1    12/2009 Kahn et al.
(Continued)

OTHER PUBLICATIONS

Lee et al., "Activity Recognition Using Hierarchial Hidden Markov Models on a Smartphone with 3D Accelerometer", Proceedings of the 6th international conference on Hybrid artificial intelligent systems, 2011. 8 pps.*

(Continued)

*Primary Examiner* — Andrew Schechter
*Assistant Examiner* — Mark I Crohn
(74) *Attorney, Agent, or Firm* — Shumaker & Sieffert, P.A.

(57) ABSTRACT

In some examples, a method includes detecting, based at least in part on sampling a first set (122) of a plurality of sensors of a computing device (110) at a first rate, an indication that the user has initiated a fitness activity (112B), wherein the computing device (110) stores pre-defined identifiers of non-fitness and fitness activities in a set of pre-defined indications of activities; responsive to detecting the indication that the user has initiated the fitness activity, sampling, at a second rate that is greater than the first rate, a second set (120) of the plurality of sensors to determine a probability that the user is engaged in the fitness activity (112B); and responsive to determining that the probability satisfies a threshold, collecting, sensor data for the fitness activity using a particular set of the plurality of sensors that corresponds to a pre-defined identifier for the fitness activity (112B).

20 Claims, 5 Drawing Sheets

(51) Int. Cl.
*A61B 5/024* (2006.01)
*A61B 5/145* (2006.01)

(56) References Cited

U.S. PATENT DOCUMENTS

| | | | |
|---|---|---|---|
| 2010/0056872 A1 | 3/2010 | Kahn et al. | |
| 2012/0316406 A1 | 12/2012 | Rahman et al. | |
| 2013/0190903 A1* | 7/2013 | Balakrishnan | A61B 5/7246 700/91 |
| 2014/0358472 A1* | 12/2014 | Goel | A61B 5/1118 702/141 |
| 2014/0358473 A1* | 12/2014 | Goel | A61B 5/1118 702/141 |
| 2016/0301581 A1* | 10/2016 | Carter | H04L 43/024 |

OTHER PUBLICATIONS

Ronao et al., "Human Activity Recognition Using Smartphone Sensors With Two-Stage Continuous Hidden Markov Models", 2014 10th International Conference on Natural Computation (ICNC). 686-691 pgs.*

Gillian, "HMM Continuous", NickGillianWiki [online]. Jan. 12, 2015. Retrieved from the Internet: <http://www.nickgillian.com/wiki/pmwiki.php/GRT/HMMContinuous> 4 pps.

Cartella et al., "Online adaptive learning of Left-Right Continuous HMM for bearings condition assessment", Jounal of Physics: Conference Series, 2012. 11 pps.

Hache et al., "Mobility Change-of-State Detection Using a Smartphone-based Approach", 2010 International Workshop on Medical Measurements and Applications Proceedings. 4 pps.

Wang et al., "A Framework of Energy Efficient Mobile Sensing for Automatic User State Recognition", Proceedings of the 7th international conference on Mobile systems, applications, and services. 2009. 14 pps.

Hardegger et al., "ActionSLAM on a Smartphone: At-Home Tracking with a Fully Wearable System", 2013 International Conference on Indoor Positioning and Indoor Navigation, Oct. 28-31, 2013. 8 pps.

Garcia et al., "Real Time Activity Recognition Using a Cell Phone's Acclerometer and Wi-Fi", Workshop Proceedings of the 8th International Conference on Intelligent Environments. 2012. 94-103 pgs.

"ActivityRecognition", Google APIs for Android, Google Developers [online]. May 28, 2015. Retrieved from the Internet: <https://developers.google.com/android/reference/com/google/android/gms/location/ActivityRecognition> 2 pps.

"ActivityRecognitionResult", Google APIs for Android, Google Developers [online]. May 28, 2015. Retrieved from the Internet: <https://developers.google.com/android/reference/com/google/android/gms/location/ActivityRecognitionResult> 4 pps.

"DetectedActivity", Google APIs for Android, Google Developers [online]. May 28, 2015. Retrieved from the Internet: <https://developers.google.com/android/reference/com/google/android/gms/location/DetectedActivity> 4 pps.

"DataType", Google APIs for Android, Google Developers [online]. May 28, 2015. Retrieved from the Internet: <https://developers.google.com/android/reference/com/google/android/gms/fitness/data/DataType> 20 pps.

"DataSet", Google APIs for Android, Google Developers [online]. May 28, 2015. Retrieved from the Internet: <https://developers.google.com/android/reference/com/google/android/gms/fitness/data/DataSet> 4 pps.

Search Report and Written Opinion of Netherlands application No. NL 1041613, dated Jun. 9, 2016, 15 pp.

* cited by examiner

UPSAMPLING SENSORS TO AUTO-DETECT A FITNESS ACTIVITY

BACKGROUND

Some mobile and wearable computing devices may track user activity to assist users in maintaining healthier and more active lifestyles. For instance, a mobile computing device may include one or more sensor components, which provide data that may be indicative of a user engaging in an activity. The mobile computing device may collect and process data from such sensor components to provide information to a user that is descriptive of the activities of the user over time.

In order to identify activities of the user, the computing device may process data from one or more of the sensor components. However, using many sensor components to identify activities of the user may adversely affect power consumption in the computing device. Conversely, using a set of only a single or few sensor components to identify an activity may adversely affect the accuracy of correctly detecting the actual activity performed by a user. As such, some computing devices may inaccurately identify a particular activity of a user and/or consume excessive amounts of power.

SUMMARY

In some examples, a method includes detecting, by a computing device of a user and based at least in part on sampling a first set of a plurality of sensors of the computing device at a first rate, an indication that the user has initiated a fitness activity, wherein the computing device stores pre-defined identifiers of non-fitness and fitness activities in a set of pre-defined indications of activities. Responsive to detecting the indication that the user has initiated the fitness activity, sampling, by the computing device in an upsampling operational state, at a second rate that is greater than the first rate, a second set of the plurality of sensors to determine a probability that the user is engaged in the fitness activity, wherein the second set of the plurality of sensors includes different sensors than the first set of the plurality of sensors. Responsive to determining that the probability satisfies a threshold, collecting, by the computing device in an active operational state that is different than the upsampling operational state, sensor data for the fitness activity using a particular set of the plurality of sensors that corresponds to a pre-defined identifier for the fitness activity in the set of pre-defined indications of activities.

In some examples, a non-transitory computer-readable storage medium is encoded with instructions that, when executed, cause at least one processor of a computing device for a user to: detect, based at least in part on sampling a first set of a plurality of sensors of the computing device at a first rate, an indication that the user has initiated a fitness activity, wherein the computing device stores pre-defined identifiers of non-fitness and fitness activities in a set of pre-defined indications of activities. The non-transitory computer-readable storage medium may also be encoded with instructions that, when executed, cause the at least one processor of the computing device to, responsive to detecting the indication that the user has initiated the fitness activity, sample, in an upsampling operational state, at a second rate that is greater than the first rate, a second set of the plurality of sensors to determine a probability that the user is engaged in the fitness activity, wherein the second set of the plurality of sensors includes different sensors than the first set of the plurality of sensors. The non-transitory computer-readable storage medium may also be encoded with instructions that, when executed, cause the at least one processor of the computing device to, responsive to determining that the probability satisfies a threshold, collect, in an active operational state that is different than the upsampling operational state, sensor data for the fitness activity using a particular set of the plurality of sensors that corresponds to a pre-defined identifier for the fitness activity in the set of pre-defined indications of activities.

In some examples, a computing device comprises: one or more computer processors; a plurality of sensors operably coupled to the one or more computer processors; and a memory comprising instructions. The instructions, when executed by the one or more computer processors, cause the one or more computer processors to: detect, based at least in part on sampling a first set of the plurality of sensors of the computing device at a first rate, an indication that a user of the computing device has initiated a fitness activity, wherein the computing device stores pre-defined identifiers of non-fitness and fitness activities in a set of pre-defined indications of activities. The instructions, when executed by the one or more computer processors, may cause the one or more computer processors to: responsive to detecting the indication that the user has initiated the fitness activity, sample, by the computing device in an upsampling operational state, at a second rate that is greater than the first rate, a second set of the plurality of sensors to determine a probability that the user is engaged in the fitness activity, wherein the second set of the plurality of sensors includes different sensors than the first set of the plurality of sensors. The instructions, when executed by the one or more computer processors, cause the one or more computer processors to: responsive to determining that the probability satisfies a threshold, collect, by the computing device in an active operational state that is different than the upsampling operational state, sensor data for the fitness activity using a particular set of the plurality of sensors that corresponds to a pre-defined identifier for the fitness activity in the set of pre-defined indications of activities.

In some examples, an apparatus comprises: means for detecting, based at least in part on sampling a first set of a plurality of sensors of the computing device at a first rate, an indication that a user of the apparatus has initiated a fitness activity, wherein the apparatus stores pre-defined identifiers of non-fitness and fitness activities in a set of pre-defined indications of activities. The apparatus may further comprise means for, responsive to detecting the indication that the user has initiated the fitness activity, sampling, by the apparatus in an upsampling operational state, at a second rate that is greater than the first rate, a second set of the plurality of sensors to determine a probability that the user is engaged in the fitness activity, wherein the second set of the plurality of sensors includes different sensors than the first set of the plurality of sensors. The apparatus may further comprise means for, responsive to determining that the probability satisfies a threshold, collecting, by the apparatus in an active operational state that is different than the upsampling operational state, sensor data for the fitness activity using a particular set of the plurality of sensors that corresponds to a pre-defined identifier for the fitness activity in the set of pre-defined indications of activities.

The details of one or more examples are set forth in the accompanying drawings and the description below. Other features, objects, and advantages of the disclosure will be apparent from the description and drawings, and from the claims.

DETAILED DESCRIPTION

Techniques of the disclosure are directed to improving the accuracy of detecting a fitness activity with lower latency by upsampling sensor components of a computing device in response to initially detecting a fitness activity. For instance, a computing device may include a set of sensor components, such as a location sensor, motion sensor, heartrate sensor and the like. To conserve power, the computing device may sample one or only a few of the sensor components at an initial, slower rate to initially detect and identify a particular activity of a user. If the computing device detects a change in activity to a fitness activity, such as transitioning from standing still to running or biking, the computing device may temporarily upsample a larger set of sensor components at a higher rate. As a consequence, the computing device uses more data from a larger set of sensor components to more accurately detect whether the user is actually engaged in the detected fitness activity. If the computing device detects a fitness activity, the computing device can temporarily generate and/or acquire a larger amount of sensor component data in a shorter period of time. By doing so, the computing device may confirm that the user is engaged in the fitness activity with less latency because the computing device may not have to wait for additional data at the slower sampling rate to confirm the user is actually engaged in the fitness activity.

If the computing device is unable to determine whether the user is engaged in the detected activity with sufficient confidence, the computing device may revert back to sampling a smaller set of sensor components at a slower rate, thereby conserving power. Alternatively, if the computing device determines with sufficient confidence that that the user is engaged in the detected fitness activity, the computing device may begin collecting fitness information for the user based on data from a set of sensor components. In this way, techniques of the disclosure may improve power use of the computing device by temporarily upsampling sensor data, while potentially detecting activities with greater accuracy and/or lower latency. Moreover, based on detecting a specific fitness activity with sufficient confidence, the techniques may collect fitness information for the user based on data from a particular set of sensor components that correspond to the specific fitness activity, thereby potentially saving power.

Figure 1:
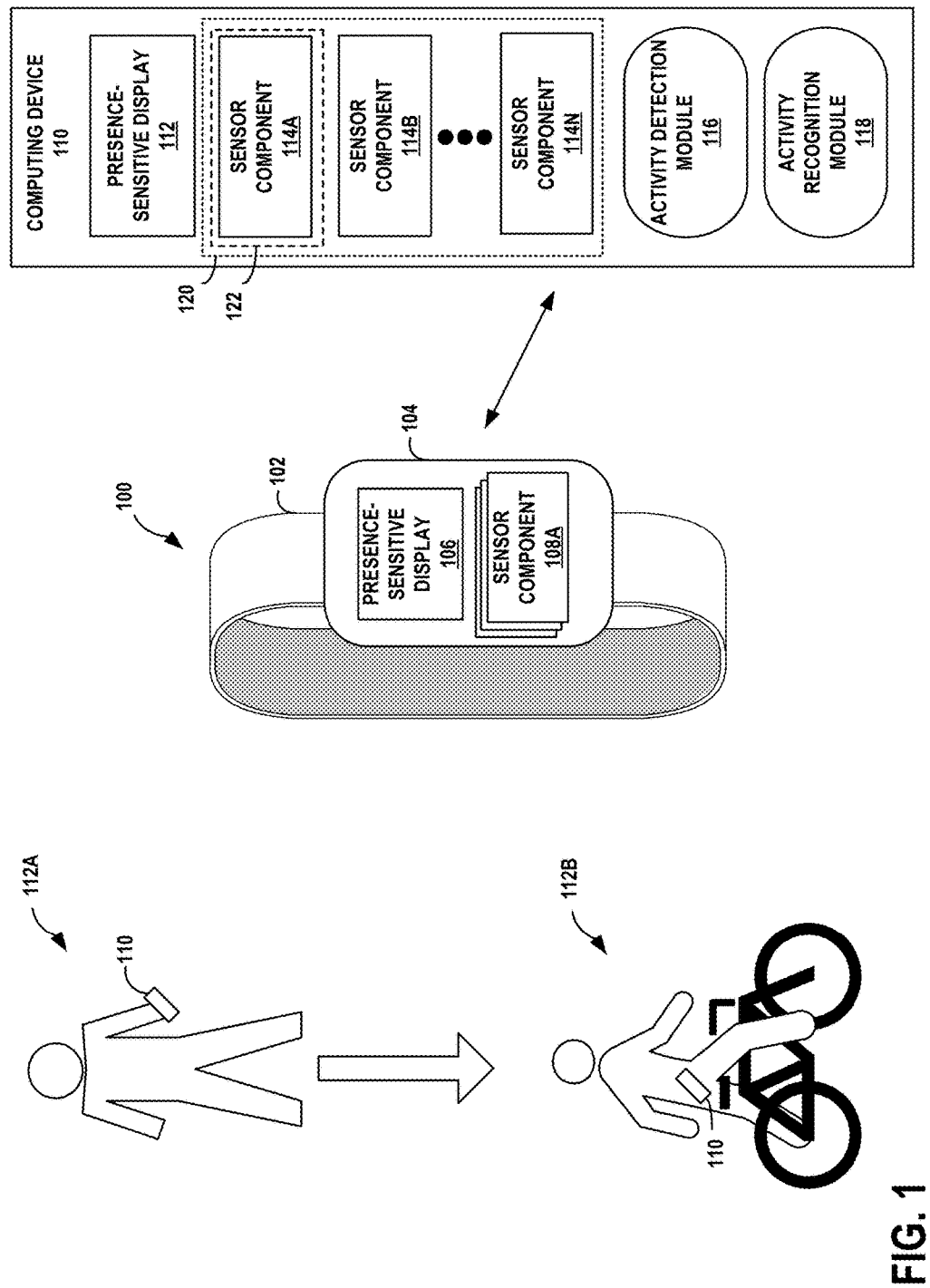
FIG. 1 is a conceptual diagram illustrating a computing device that may detect a fitness activity with lower latency and/or greater accuracy by upsampling one or more sensors, in accordance with one or more aspects of the present disclosure.

FIG. 1 is a conceptual diagram illustrating a computing device 110 that may detect a fitness activity with lower latency and/or greater accuracy by upsampling one or more sensors, in accordance with one or more aspects of the present disclosure. As shown in FIG. 1, computing device 110 may be a smartphone. In some examples, computing device 110 may be a laptop computer, a tablet computer, an e-book reader computing device, an in-vehicle computing device (e.g., an automobile console computing device), a fitness equipment computing device (e.g., a bike-mounted computing device), a head-mounted computing device, or any other computing device suitable for detecting an activity of a user.

In some examples, computing device 110 may include a presence-sensitive display 112. Presence-sensitive display 112 of computing device 110 may function as an input device for computing device 110 and as an output device. Presence-sensitive display 112 may be implemented using various technologies. For instance, presence-sensitive display 112 may function as an input device using a presence-sensitive input component, such as a resistive touchscreen, a surface acoustic wave touchscreen, a capacitive touchscreen, a projective capacitance touchscreen, a pressure-sensitive screen, an acoustic pulse recognition touchscreen, or another presence-sensitive display technology. Presence-sensitive display 112 may function as an output (e.g., display) device using any one or more display components, such as a liquid crystal display (LCD), dot matrix display, light emitting diode (LED) display, organic light-emitting diode (OLED) display, e-ink, or similar monochrome or color display capable of outputting visible information to a user of computing device 110.

Computing device 110 may also include one or more sensor components 114A-114N ("sensor components 114"). In some examples, a sensor component may be an input component that obtains environmental information of an environment that includes computing device 110. A sensor component may be an input component that obtains physiological information of a user of computing device 110. In some examples, a sensor component may be an input component that obtains physical position, movement, and/or location information of computing device 110. For example, sensor components 114 may include, but are not limited to: movement sensors (e.g., accelerometers), temperature sensors, position sensors (e.g., a gyro), pressure sensors (e.g., a barometer), proximity sensors (e.g., an inferred sensor), ambient light detectors, heart-rate monitors, location sensors (e.g., Global Positioning System sensor), or any other type of sensing component. Other examples of sensor components are described in FIG. 2. As further described in this disclosure, activity recognition module 118 may determine one or more user activities based on raw sensor data generated by one or more of sensor components 114.

In some examples, computing device 110 may be communicatively coupled to a wearable computing device 100. For instance, computing device 110 may use one or more communication protocols to send and receive data with wearable computing device 100. In some example examples, communication protocols may include Bluetooth, Near-Field Communication, Wi-Fi, or any other suitable communication protocol.

In the example of FIG. 1, wearable computing device 100 is a computerized watch. However in other examples, wearable computing device 100 ("wearable 100")) is a computerized fitness band/tracker, computerized eyewear, computerized headwear, a computerized glove, etc. In other examples, wearable 100 may be any type of mobile computing device that can attach to and be worn on a person's body or clothing. For example, wearable 100 may be any tablet computer, mobile phone, personal digital assistant (PDA), game system or controller, media player, e-book reader, television platform, navigation system, remote control, or other mobile computing device that can easily be moved by a user in accordance with the below described techniques.

As shown in FIG. 1, in some examples, wearable 100 may include attachment component 102 and electrical housing 104. Housing 104 of wearable 100 includes a physical portion of a wearable computing device that houses a combination of hardware, software, firmware, and/or other electrical components of wearable 100. For example, FIG. 1 shows that within housing 104, wearable computing device 100 may include sensor components 108A-108N ("sensor components 108") and presence-sensitive display 106. Presence-sensitive display 106 may be a presence-sensitive display as described with respect to presence-sensitive display 112, and sensor components 108 may be sensor components as described with respect to sensor components 114. Housing 104 may also include other hardware components and/or software modules not show in FIG. 1, such as one or more processors, memories, operating systems, applications, and the like.

Attachment component 102 may include a physical portion of a wearable computing device that comes in contact with a body (e.g., tissue, muscle, skin, hair, clothing, etc.) of a user when the user is wearing wearable computing device 100 (though, in some examples, portions of housing 104 may also come in contact with the body of the user). For example, in cases where wearable computing device 100 is a watch, attachment component 102 may be a watch band that fits around a user's wrist and comes in contact with the skin of the user. In examples where wearable computing device 100 is eyewear or headwear, attachment component 102 may be a portion of the frame of the eyewear or headwear that fits around a user's head, and when wearable computing device 100 is a glove, attachment component 102 may be the material of the glove that conforms to the fingers and hand of the user. In some examples, wearable computing device 100 can be grasped and held from housing 104 and/or attachment component 102.

As shown in FIG. 1, computing device 110 may include activity recognition module 118. Activity recognition module 118 may determine one or more activities of a user based on raw sensor data generated by one or more of sensor components 114. For instance, activity recognition module 118 maintain a set one or more pre-defined identifiers that each respectively correspond to a different user activity. In some examples, the pre-defined identifiers may be enumerated values that correspond to different user activities, while in other examples, activity recognition module 118 may use any other suitable type of value (e.g., string, integer, and the like). Activities detected by activity recognition module 118 may include but are not limited to: riding in a vehicle, riding on a bicycle, moving on foot, running, remaining still (e.g., not moving), tiling or otherwise changing the angle of computing device 110 relative to gravity, or walking. Activity recognition module 118 may store pre-defined identifiers that each correspond to a respective activity, such as IN_VEHICLE, ON_BICYCLE, ON_FOOT (e.g., walking or running), RUNNING, STILL (e.g., device is still/not moving), TILTING (e.g., device angle relative to a reference, such as gravity, has changed more than a threshold amount), and WALKING. In some examples, activity recognition module 118 may also maintain a pre-defined identifier, such as UNKNOWN, which corresponds to an activity that is not recognized or identifiable by activity recognition module 118.

In some examples, activities may be categorized into subsets, such as fitness activities and non-fitness activities. A fitness activity may be an activity that elevates a user's heartrate above a resting heartrate and/or requires physical effort that is carried out to sustain or improve health and fitness. Examples of fitness activities include, but are not limited to: biking, walking, running, weight-lifting, calisthenics, to name only a few examples. A non-fitness activity may be an activity that does not elevate a user's heartrate above a resting heartrate and/or does not require physical effort that is carried out to sustain or improve health and fitness. Examples of non-fitness activities include, but are not limited to: riding in a vehicle, standing/sitting/laying, or a device remaining still. In some examples, activity recognition module 118 and/or activity detection module 116 may store information that indicates whether a predefined identifier for an activity is a fitness activity, a non-fitness activity, or an unknown activity.

Although activity recognition module 118 and activity detection module 116 are described as implemented and operating at computing device 110 for example purposes, wearable computing device 100 may also implement and/or operate an activity recognition module and/or activity detection module that include functionality described with respect to activity recognition module 118 and activity detection module 116 of computing device 110. In some examples, an activity recognition module and/or activity detection module implemented and/or operating at wearable computing device 100 may send and receive information (e.g., activity recognition results ("ARRs"), raw sensor component data, and the like) with activity recognition module 118 and activity detection module 116 via wired or wireless communication. Activity recognition module 118 and activity detection module 116 may use such information received from wearable computing device 100 in accordance with techniques of the disclosure, as though the information were generated locally at computing device 110.

Activity recognition module 118 may receive raw sensor data that correspond to one or more of sensor components 114 and determine one or more activities that the user is engaged in. For instance, activity recognition module 118 may receive raw sensor data from sensor processing modules (e.g., as further described in FIG. 2). Sensor processing modules may provide interfaces between hardware that implement sensor components 114 and modules, such as activity recognition module 118, that further process the raw sensor data. For example, a sensor processing module may generate raw sensor data that represent or otherwise correspond to outputs of hardware that implement a particular sensor component. As an example, a sensor processing module for a GPS sensor component may generate raw sensor data that includes latitude and longitude values. As another example, a sensor processing module for an accelerometer sensor component may generate raw sensor data that includes acceleration values along different axes of a coordinate system.

Activity recognition module 118 may use one or more known techniques to identify an activity of a user based on raw sensor data. Examples of such activity recognition techniques include k-nearest neighbor, Hidden Markov Models, decision trees, bag of features, Bayesian classifiers, support vector machine classifiers, and machine learning, to name only a few examples. Activity recognition module 118 may maintain one or more models that are based on a particular activity recognition technique. Initially, activity recognition module 118 may train the model based on instances of raw sensor data that correspond to known user activities. For instance, a user that engages in a particular activity may cause a computing device to generate a particular collection of raw sensor data over a period of time. Activity recognition module 118 may train the one or more models based on one or more collections of raw sensor data that correspond to respective activities. In this way, if activity recognition module 118 later receives a collection of raw sensor data that corresponds to a particular activity, activity recognition module 118 may correctly identify the particular activity.

Activity recognition module 118 may generate, based on the raw sensor data, one or more probabilities that correspond to one or more user activities. That is, activity recognition module 118 may, for raw sensor data at a particular period in time, generate respective probabilities for respective user activities. Activity recognition module 118 may use raw sensor data generated by one or more of sensor components 114, one or more of sensor components 108, and/or a combination of any of sensor components 114 and sensor components 108. As an example, activity recognition module 118 may, for raw sensor data generated at or over a particular period in time, generate a probability of 0.5 that the user is WALKING, a probability of 0.3 that the user is RUNNING, and a probability of 0.2 that the activity that the user is engaged in UNKNOWN (e.g., an unknown activity). In some examples, activity recognition module 118 may generate an activity recognition result (ARR) that includes activity-probability pairs, which are based on raw sensor data at or during a particular period in time. In some examples, an ARR may be implemented as an object. For purposes of this disclosure an object may refer to a data structure, variable or particular instance of a class in object-oriented programming that includes variables and/or functions.

In some examples, activity recognition module 118 may provide one or more application programming interfaces (APIs) that are accessible to other modules of computing device 110. For instance, activity detection module 116 may call or otherwise invoke one or more APIs of activity recognition module 118 to receive ARRs. In some examples, activation recognition module 118 may be implemented as a service, which other modules may utilize. For instance, activity detection module 116 may register with activity recognition module 118 to receive ARRs. In some examples, activity recognition module 118 may periodically and/or asynchronously push ARRs to activity detection module 116 as the ARRs are generated by activity recognition module 116. In other examples, activity detection module 116 may periodically and/or asynchronously poll activity recognition module 118 for ARRs.

As shown in FIG. 1, computing device 110 may include activity detection module 116. Activity detection module 116 may determine or otherwise identify a particular activity that the user is performing based on a set of ARRs over time, rather than determining the particular activity based on a single ARR. Based on identifying the particular activity, activity detection module 116 may cause computing device 110 to perform one or more operations specific to the particular activity, such as collecting specific data from specific sensors for the particular activity.

Activity detection module 116 may periodically determine what activity the user is performing based on a set of ARRs over a period of time. For instance, activity detection module 116 may register with activity recognition module 118 to receive ARRs or periodically poll activity recognition module 114 to receive ARRs. In either case, activity detection module 116 may collect or otherwise receive an ARR at a particular rate (e.g., 1 ARR per minute). For instance, activity detection module 116 may receive an ARR every minute from activity recognition module 118. Activity detection module 116 may store a defined quantity of ARRs, which activity detection module 116 further processes to determine which activity the user is engaged in. For example, activity detection module 116 may store the most recent 30 ARRs in a cyclic buffer. The defined quantity may be based on a maximum count of ARRs to store and/or a maximum time duration (e.g., 30 minutes) to retain ARRs from the time that the ARRs are created.

In some examples, activity detection module 116 may use each ARR included in a defined quantity of ARRs to determine which activity the user is engaged in over a recent period of time. Activity detection module 116 may, for instance, determine respective aggregate probabilities for respective activities using one or more techniques. For instance, activity detection module 116 may determine, for each activity, an average of the probabilities for the activity in each of the ARRs in the set of ARRs. As an example, activity detection module 116 may average the probability for walking in each ARR of a set of ARRs to determine the aggregate probability for walking. As another example, activity detection module 116 may periodically run a Hidden Markov Model (HMM) transformation on a defined quantity of ARRs. In some examples, the HMM transformation may indicate which activity the user is engaged in over a recent period of time. For instance, the HMM transformation may indicate which activity the user was engaged in over the longest period of time based on the defined quantity of ARRs. In some examples, the HMM transformation may indicate one or more probabilities for one or more respective activities, where each respective probability indicates a likelihood of a user performing the activity.

Activity detection module 116 may apply, as an HMM transformation, one or more techniques, such as one or more known forward-backward algorithms that compute posterior marginal distributions for an HMM in two passes—one pass evaluating ARRs forward in time to determine probabilities for respective activities, and the second pass evaluating ARRs backward in time to determine probabilities for respective activities. Each state in the HMM may represent a different activity, and as such, activity detection module 116 may determine probabilities for different activities based on the probabilities generated using a forward-backward algorithm for different states.

In either of the averaging and HMM techniques, activity detection module 116 is able to determine which activity the user is most likely engaged in over a recent period of time (e.g., for the defined quantity of ARRs). In some examples, the activity that the user is most likely engaged in for the defined quantity of ARRs may be referred to as the identified activity. For instance, activity detection module 116 may determine that the identified activity is the activity with the highest respective probability. In another example, activity detection module 116 may determine that the identified activity is the activity that the user was engaged in most frequently over a particular period of time. As described above, based on determining the identified activity, activity detection module 116 may cause computing device 110 to perform one or more operations specific to the identified activity, such as collecting specific data from specific sensors for the identified activity.

To conserve power, activity recognition module 118 may generate ARRs based raw sensor data from one or only a few of the total number of available sensor components 114. Activity recognition module 118 may conserve power by reducing the sampling rate with which it receives raw sensor data from a set of one or more of sensor components 114. For instance, activity recognition module 118 may generate ARRs based on raw sensor data from an accelerometer sensor component without using any other of the available sensor components 114 to generate the ARRs. However, the raw sensor data for the accelerometer sensor component that is collected by the activity recognition module 118 may be sparse and/or may not have enough information or resolution to generate ARRs that enable activity detection module 116 to determine the user's identified activity with high-accuracy and/or low-latency. As a result, activity detection module 116 may be unable to detect an identified fitness activity and may fail to perform one or more operations for the identified fitness activity, such as recording fitness information for the user's activity. For instance, a 5 minute delay in detecting a user's bike ride may lead to a loss of recording user's biking distance for the initial 5 minutes.

Activity detection module 116 implements techniques that may improve the accuracy and/or reduce the latency with which activity detection module 116 determines that a user is engaged in an identified fitness activity. Rather than continuously sampling all sensor components all the time (which may consume large amounts of power) or only infrequently sampling a single sensor to detect an identified fitness activity (which may have low accuracy and/or high latency), techniques of the disclosure may upsample a larger set of sensors at a higher rate for a defined period of time if activity detection module 116 determines that a user may have initiated engagement in a fitness activity. In this way, activity detection module 116 may initially sample a smaller set of sensor components at a lower rate to preliminarily detect whether a user has begun a fitness activity, and if it is likely that the user has begun a fitness activity, activity detection module 116 may then upsample a larger set of sensors at a higher rate for a defined period of time to confirm with higher confidence that the user is actually engaged in an identified fitness activity.

To improve the accuracy and/or reduce the latency for detecting a fitness activity, activity detection module 116 may implement a state machine. The state machine may have multiple states. Each state may cause computing device 110 to perform a set of operations that are particular to the respective state. For instance, activity detection module 116 may implement a state machine, as further described in FIG. 3, which includes three states: a Normal State, an Upsampling State, and an Active State.

In some examples, activity detection module 116 may initially operate in the Normal State. In some examples, the Normal State may correspond to a state in which the user is not performing a fitness activity. For instance, the user may be walking or still in the Normal State. In the Normal State, activity detection module 116 may receive ARRs from activity recognition module 118 at a "normal rate." The normal rate may be a pre-defined rate that is set by a user or hard-coded into activity detection module 116. Examples of normal rates may include receiving one ARR per 30 seconds, one ARR per minute, one ARR per 5 minutes, to name only a few examples. While activity detection module 116 operates in the Normal State, activity detection module 116 may, as described above, apply one or more techniques described above (e.g., averaging or HMM transformations) to a defined quantity of ARRs in order to determine which activity the user is engaged in over a recent period of time. For instance, while operating in the Normal State, activity detection module 116 may perform an HMM transformation on the most recent 30 ARRs that were received once per minute over a 30 minute interval.

In the Normal State, activity recognition module 118 may generate ARRs based on a "normal state set" of sensor components 122, rather than all of the sensors components available to activity recognition module 118. For instance, a normal state set of sensor components 122 may include an accelerometer sensor component, but may exclude other sensor components available to activity recognition module 118. In this way, while operating in the Normal State, techniques of the disclosure may save power by generating ARRs with relatively fewer sensor components than the Upsampling State and at a relatively lower sampling rate than the Upsampling State.

Based on applying one or more techniques described above (e.g., averaging or HMM transformations) to a defined quantity of ARRs, activity detection module 116 may determine that the user has transitioned from a non-fitness activity to a fitness activity. For instance, activity detection module 116 may determine, based at least in part on sampling the normal state set of sensor components 122 at the normal rate, an indication that the user has transitioned from a non-fitness activity to a fitness activity. As an example, activity detection module 116 may store information of the highest probability activity over a past period of time. The highest probability over a past period of time may correspond to a non-fitness activity 112A, such as remaining still. If the user later transitions to a fitness activity 112B, such as biking, activity detection module 116 may determine, in the Normal State, that the identified user activity is biking. For instance, activity detection module 116 may determine that the highest probability activity has changed from non-fitness activity 112A to fitness activity 112B. In some examples, the probability for the highest probability activity may satisfy a threshold (e.g., greater than the threshold). For instance, the threshold may be equal to the second highest probability, and the probability for the highest probability activity may be greater than the threshold.

As described above, the indication that the user has transitioned from a non-fitness activity to a fitness activity may be a probability of an activity, such as a fitness activity. In some examples, the indication that the user has transitioned from a non-fitness activity to a fitness activity may be a change in the identified activity, such as from a non-fitness activity to a fitness activity. For instance, activity detection module 116 may receive an ARR that indicates a TILT or ON_BICYCLE activity that has the highest probability among probabilities for different possible user activities. In some examples, the indication that the user has transitioned from a non-fitness activity to a fitness activity may be an ARR that indicates an UNKNOWN activity that has the highest probability among probabilities for different possible user activities, which may indicate that additional raw sensor data is need to more accurately determine an identified user activity.

Activity detection module 116, in response to determining the indication that the user has changed from non-fitness activity 112A to fitness activity 112B, may transition from the Normal State to the Upsampling State. In the Upsampling State, activity detection module 116 may cause computing device 110 to sample an "upsampling state set" of sensor components 120 at a "sensor upsampling" rate. In some examples, the "upsampling state set" of sensor components 120 and/or the "sensor upsampling" rate may be activity-specific. That is, the particular sensor components in the upsampling state set may be different for different activities. The particular sensor upsampling rate for a particular sensor component in the upsampling state set may be different for different activities. In examples where the upsampling state set of sensor components 120 and/or the sensor upsampling rate are activity-specific, activity detection module 116 may, when transitioning from the Normal State to the Upsampling State, store, send, or otherwise use an identifier of the fitness activity detected in the Normal State to select the upsampling state set of sensor components 120 and/or the sensor upsampling rate for the particular fitness activity.

The upsampling state set of sensor components 120 may include a greater number of sensor components than the normal state set of sensor components 122 as specified by the Normal State. For instance, the upsampling state set of sensor components 120 may include all sensor components available to activity detection module 116, such as sensor components 114 and sensor components 108. In some examples, the upsampling state set of sensor components 120 may include subset of all sensor components available to activity detection module 116 with a cardinality that is greater than the normal state set of sensor components 122. The upsampling state set of sensor components 120 may include different subset of all sensor components available to activity detection module 116 than the normal state set of sensor components 122.

In some examples, the sensor upsampling rate may be a faster or higher rate than the normal rate specified by the Normal State. By sampling the larger upsampling state set sensor components 120 and at the higher sensor upsampling rate, activity recognition module 118 may generate ARRs at a higher rate, and the ARRs are received by activity detection module 116. By sampling more sensor components at a higher rate, the Upsampling State may result in more ARRs that indicate with greater accuracy which activity the user is engaged in. As such, activity detection module 116 may not have to wait for additional ARRs at the slower normal sampling rate before detecting a fitness activity with sufficient confidence, thereby lowering the latency to detect the fitness activity. As a result, rather than requiring 3-4 minutes of sampling ARRs at the normal rate in a 15 minute run to determine whether a user has engaged in running, techniques of the disclosure may detect that the user is running in a shorter period of time, such as 30 seconds to a minute, as an example. As further described in FIG. 2, in addition to receiving ARRs at a higher rate, activity detection module 116 may receive raw sensor component data to further improve the detection and identification of a particular fitness activity.

In some examples, activity detection module 116 may operate in the Upsampling State for a defined period of time. The defined period of time may be a hard-coded value, a value set by a user, or a value that dynamically changes. For example, activity detection module 116 may operate in the Upsampling State for a defined period of time of 30 seconds. While operating in the Upsampling State, activity detection module 116 may receive 5 ARR samples in a 30 second interval. As such, activity detection module 116 may receive ARRs at the higher sensor upsampling rate, and the ARRs may be generated by activity recognition module 118 based on the larger upsampling state set of sensor components 120.

While operating in the Upsampling State, activity detection module 116 may use at least the ARRs generated by activity recognition module 118 during the Upsampling State to determine which activity the user is engaged in over a recent period of time. Activity detection module 116 may, during the Upsampling State, determine respective aggregate probabilities for respective activities using one or more techniques. For instance, activity detection module 116 may determine, for each activity, an average of the probabilities for the activity in each of the ARRs in the set of ARRs. As another example, activity detection module 116 may run a HMM transformation on two or more of the ARRs generated by activity recognition module 118 while operating in the Upsampling State. In some examples, the HMM transformation may indicate which activity the user is engaged in over a recent period of time. For instance, the HMM transformation may indicate which activity the user was engaged in over the longest period of time based on the defined quantity of ARRs. In some examples, the HMM transformation may indicate one or more probabilities for one or more respective activities, where each respective probability indicates a likelihood of a user performing the activity.

Activity detection module 116 may determine whether a probability for a fitness activity satisfies a threshold (e.g., a probability is greater than, greater than or equal to, less than, less than or equal to, or equal to the threshold). The threshold may be a hard-coded value, a value set by a user, or a value that dynamically changes. In some examples, activity detection module 116 may store or otherwise use different thresholds for different activities. In any case, activity detection module 116, while operating in the Upsampling State, may determine whether a probability for the threshold activity satisfies a threshold. In some examples, if none of the respective probabilities for the respective probabilities satisfies a threshold, then activity detection module 116 may revert operation back to the Normal State.

In other examples, if none of the respective probabilities for the respective activities satisfies a threshold, activity detection module 116 may remain in the Upsampling State for an additional defined period of time, as described above, that activity detection module 116 operates in the Upsampling State. That is, activity detection module 116 may continue or otherwise repeat operation in the Upsampling State again for the defined period of time. As an example, activity detection module 116 may remain in the Upsampling State for an additional 30 seconds, where 30 seconds is the defined period of time. Activity detection module 116 may remain in the Upsampling State for a defined number of intervals (where the intervals are equal to the defined period of time), if none of the respective probabilities for the respective probabilities satisfies a threshold. If, after the defined number of intervals, none of the respective probabilities for the respective probabilities satisfies a threshold, then activity detection module 116 may revert to operation in the Normal State.

In some examples, while operating in the Upsampling State, activity detection module 116 may determine that a probability for a fitness activity satisfies a threshold. As such, activity detection module 116 may determine that it is likely that the user is engaged in the particular fitness activity. Activity detection module 116 may transition to an Active State that is different than the Upsampling State.

In the Active State, activity detection module 116 may sample an "active state set" of sensor components at an "active sampling" rate. The active state set of sensor components may include a different number of sensor components than the normal state set and/or upsampling state set of sensor components. In some examples, different active state sets of sensor components may correspond to different fitness activities. That is, activity detection module 116 may maintain mappings or other associations between sets of sensors and particular fitness activities. For instance, activity detection module 116 may include a mapping between an ON_BICYCLE fitness activity and a set of sensor components that include: a motion sensor, a location sensor (e.g., GPS), temperature sensor, and altitude sensor. Activity detection module 116 may include a separate mapping between an ON_STATIONARY_BIKE fitness activity and a set of sensor components that include: a motion sensor but not a location sensor, temperature sensor, and altitude sensor. As such, activity detection module 116 may, when transitioning from the Upsampling State to the Activity State, "back off" or otherwise stop using one or more sensor components that do not provide information that is relevant or useful for generating fitness information for the particular fitness activity and/or detecting the particular fitness activity.

Activity detection module 116, when transitioning from the Upsampling State to the Active State, may store, send, or otherwise use an identifier of the fitness activity to select the set of sensors for a particular fitness activity. The identifier may be a pre-defined identifier for the fitness activity in the set pre-defined indications of activities, such as ON_BICYCLE. In this way, activity detection module 116 may collect data from a set of sensors that are tailored to or are otherwise specific or relevant to the detected fitness activity. In some examples, the active sampling rate when collecting data from one or more of sensors components 114 may be a rate that is different than the normal and/or sensor upsampling rates specified by the Normal State and Upsampling States, respectively. For instance, the active sampling rate may be a rate that is greater than or less than the normal and/or sensor upsampling rates specified by the Normal State and Upsampling States.

Figure 2:
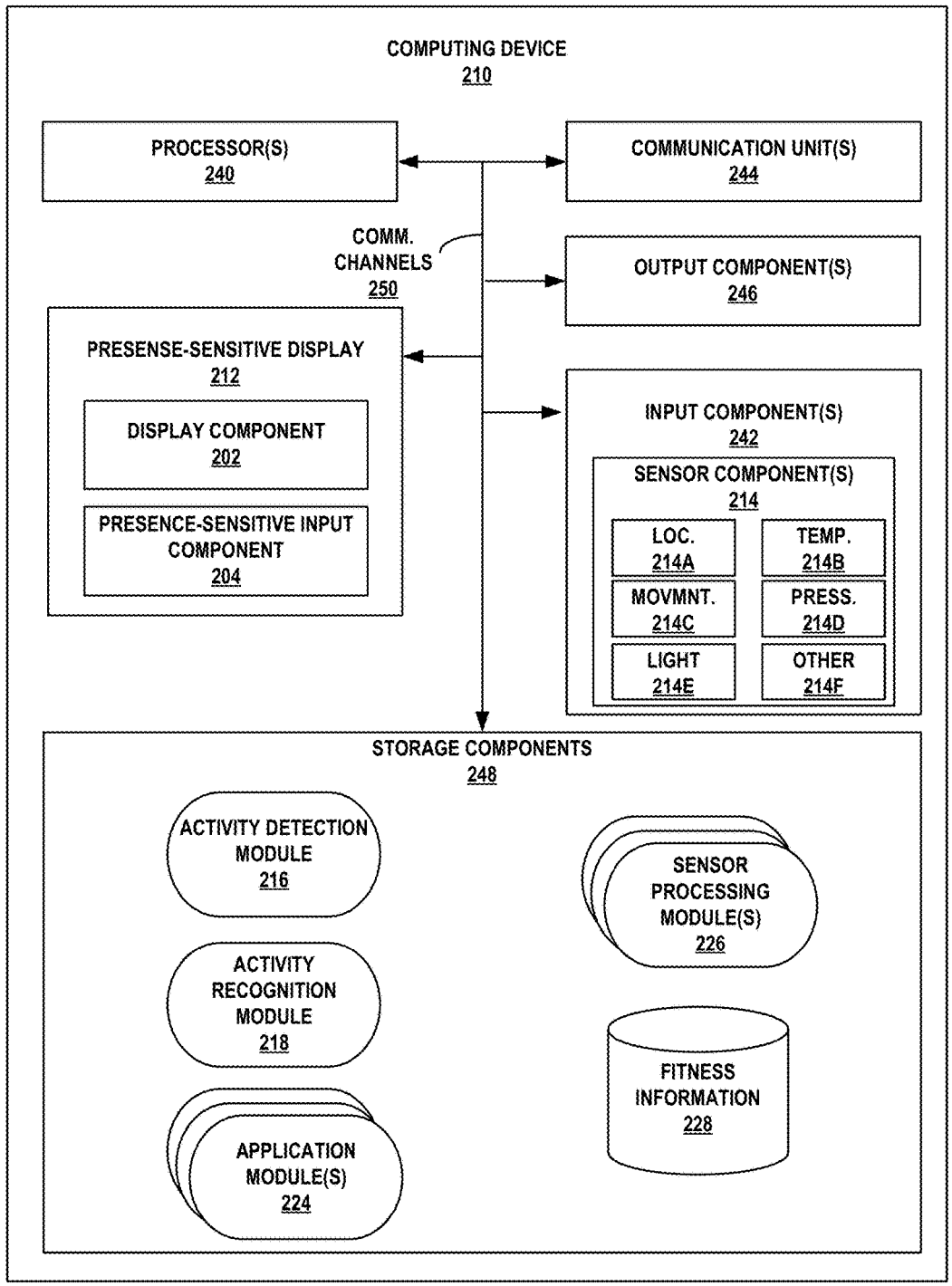
FIG. 2 is a block diagram illustrating further details of a computing device that may detect a fitness activity with lower latency and/or greater accuracy by upsampling one or more sensors, in accordance with one or more aspects of the present disclosure.

In some examples, activity detection module 116 may collect data from the set of sensors and store the data as fitness information (e.g., fitness information 228 as shown in FIG. 2). Fitness information may include data descriptive of a particular fitness activity. Examples of such data include but are not limited to: time of fitness activity, geographic locations at which user performs the fitness activity, heart-rate, number of steps taken by a user, speed or rate of change at which a user is moving, temperature of the user or the environment of the user, altitude or elevation at which the user performs the activity, to name only a few examples of fitness information. In some examples, activity detection module 116 may output the fitness information to the user in a graphical user interface. In some examples, activity detection module 116 may perform analytics on the fitness information such as determining various statistical metrics including aggregate values, average values, and the like. In some examples, activity detection module 116 may send the fitness information to a remote server that associates the fitness information with a user account of the user. In still other examples, activity detection module 116 may, upon detecting that the user has transitioned into the Active State, may notify one or more third-party applications. For instance, a third-party fitness application may register with activity detection module 116, and the third-party fitness application can record fitness information for a user while activity detection module 116 is operating in the Active State. For example, when activity detection module 116 transitions into and out of the Active State, activity detection module 116 may notify the third-party fitness application.

In some examples, activity detection module 116 remains in the Active State until activity detection module 116 determines that a change in activity has occurred. For instance, activity detection module 116, while in the Activity State, may continue to receive ARRs from activity recognition module 118. If activity detection module 116 determines, based on one or more ARRs, that the user has changed from a current fitness activity to a different activity, then activity detection module 116 may transition back to the Upsampling State to determine whether the user has actually changed from the current fitness activity to a different activity. In some examples, activity detection module 116 may determine that the user has changed from a current fitness activity to a different activity if the ARR indicates that the highest probability activity in the ARR is different than the current fitness activity for which activity detection module 116 is collecting fitness information in the Active State. In some examples, if activity detection module 116 detects an indication of a different activity than the current fitness activity, then activity detection module 116 may transition to the Upsampling State. Transitions between the Normal, Upsampling, and Active states are further described in FIG. 3.

FIG. 2 is a block diagram illustrating further details of a computing device 210 that may detect a fitness activity with lower latency and/or greater accuracy by upsampling one or more sensors, in accordance with one or more aspects of the present disclosure. Computing device 210 of FIG. 2 is described below as an example of computing device 110 illustrated in FIG. 1. FIG. 2 illustrates only one particular example of computing device 210, and many other examples of computing device 210 may be used in other instances and may include a subset of the components included in example computing device 210 or may include additional components not shown in FIG. 2.

As shown in the example of FIG. 2, computing device 210 includes presence-sensitive display 212, one or more processors 240, one or more input components 242, one or more communication units 244, one or more output components 246, and one or more storage components 248. Presence-sensitive display (PSD) 212 includes display component 202 and presence-sensitive input component 204. Input components 242 include sensor components 214. Storage components 248 of computing device 210 also include activity detection module 216, activity recognition module 218, application modules 224, sensor processing modules 226, and fitness information datastore 228.

Communication channels 250 may interconnect each of the components 240, 212, 202, 204, 244, 246, 242, 214, 248, 216, 218, 224, 226, and 228 for inter-component communications (physically, communicatively, and/or operatively). In some examples, communication channels 250 may include a system bus, a network connection, an inter-process communication data structure, or any other method for communicating data.

One or more input components 242 of computing device 210 may receive input. Examples of input are tactile, audio, and video input. Input components 242 of computing device 210, in one example, includes a presence-sensitive display, touch-sensitive screen, mouse, keyboard, voice responsive system, video camera, microphone or any other type of device for detecting input from a human or machine.

One or more input components 242 include one or more sensor components 214. Numerous examples of sensor components 214 exist and include any input component configured to obtain environmental information about the circumstances surrounding computing device 210 and/or physiological information that defines the activity state and/or physical well-being of a user of computing device 210. In some examples, a sensor component may be an input component that obtains physical position, movement, and/or location information of computing device 210. For instance, sensor components 214 may include one or more location sensors 214A (GPS components, Wi-Fi components, cellular components), one or more temperature sensors 214B, one or more movement sensors 214C (e.g., accelerometers, gyros), one or more pressure sensors 214D (e.g., barometer), one or more ambient light sensors 214E, and one or more other sensors 214F (e.g., microphone, camera, infrared proximity sensor, hygrometer, and the like). Other sensors may include a heart rate sensor, magnetometer, glucose sensor, hygrometer sensor, olfactory sensor, compass sensor, step counter sensor, to name a few other non-limiting examples.

One or more output components 246 of computing device 210 may generate output. Examples of output are tactile, audio, and video output. Output components 246 of computing device 210, in one example, includes a presence-sensitive display, sound card, video graphics adapter card, speaker, cathode ray tube (CRT) monitor, liquid crystal display (LCD), or any other type of device for generating output to a human or machine.

One or more communication units 244 of computing device 210 may communicate with external devices via one or more wired and/or wireless networks by transmitting and/or receiving network signals on the one or more networks. Examples of communication units 244 include a network interface card (e.g. such as an Ethernet card), an optical transceiver, a radio frequency transceiver, a GPS receiver, or any other type of device that can send and/or receive information. Other examples of communication units 244 may include short wave radios, cellular data radios, wireless network radios, as well as universal serial bus (USB) controllers.

Presence-sensitive display (PSD) 212 of computing device 200 includes display component 202 and presence-sensitive input component 204. Display component 202 may be a screen at which information is displayed by PSD 212 and presence-sensitive input component 204 may detect an object at and/or near display component 202. As one example range, presence-sensitive input component 204 may detect an object, such as a finger or stylus that is within two inches or less of display component 202. Presence-sensitive input component 204 may determine a location (e.g., an (x,y) coordinate) of display component 202 at which the object was detected. In another example range, presence-sensitive input component 204 may detect an object six inches or less from display component 202 and other ranges are also possible. Presence-sensitive input component 204 may determine the location of display component 202 selected by a user's finger using capacitive, inductive, and/or optical recognition techniques. In some examples, presence-sensitive input component 204 also provides output to a user using tactile, audio, or video stimuli as described with respect to display component 202. In the example of FIG. 2, PSD 212 presents a user interface.

While illustrated as an internal component of computing device 210, presence-sensitive display 212 may also represent and external component that shares a data path with computing device 210 for transmitting and/or receiving input and output. For instance, in one example, PSD 212 represents a built-in component of computing device 210 located within and physically connected to the external packaging of computing device 210 (e.g., a screen on a mobile phone). In another example, PSD 212 represents an external component of computing device 210 located outside and physically separated from the packaging of computing device 210 (e.g., a monitor, a projector, etc. that shares a wired and/or wireless data path with a tablet computer).

PSD 212 of computing device 210 may receive tactile input from a user of computing device 110. PSD 212 may receive indications of the tactile input by detecting one or more gestures from a user of computing device 210 (e.g., the user touching or pointing to one or more locations of PSD 212 with a finger or a stylus pen). PSD 212 may present output to a user. PSD 212 may present the output as a graphical user interface, which may be associated with functionality provided by computing device 210. For example, PSD 212 may present various user interfaces of components of a computing platform, operating system, applications, or services executing at or accessible by computing device 210 (e.g., an electronic message application, a navigation application, an Internet browser application, a mobile operating system, etc.). A user may interact with a respective user interface to cause computing devices 210 to perform operations relating to a function.

PSD 212 of computing device 210 may detect two-dimensional and/or three-dimensional gestures as input from a user of computing device 210. For instance, a sensor of PSD 212 may detect a user's movement (e.g., moving a hand, an arm, a pen, a stylus, etc.) within a threshold distance of the sensor of PSD 212. PSD 212 may determine a two or three dimensional vector representation of the movement and correlate the vector representation to a gesture input (e.g., a hand-wave, a pinch, a clap, a pen stroke, etc.) that has multiple dimensions. In other words, PSD 212 can detect a multi-dimension gesture without requiring the user to gesture at or near a screen or surface at which PSD 212 outputs information for display. Instead, PSD 212 can detect a multi-dimensional gesture performed at or near a sensor which may or may not be located near the screen or surface at which PSD 212 outputs information for display.

One or more processors 240 may implement functionality and/or execute instructions within computing device 210. For example, processors 240 on computing device 210 may receive and execute instructions stored by storage components 248 that execute the functionality of modules 216, 218, 224, 226, and/or 228. The instructions executed by processors 240 may cause computing device 210 to store information within storage components 248 during program execution. Examples of processors 240 include application processors, display controllers, sensor hubs, and any other hardware configure to function as a processing unit. Processors 240 may execute instructions of modules 216, 218, 224, 226, and/or 228 to cause PSD 212 to render portions of content of display data as one of user interface screen shots at PSD 212. That is, modules 216, 218, 224, 226, and/or 228 may be operable by processors 240 to perform various actions or functions of computing device 210.

One or more storage components 248 within computing device 210 may store information for processing during operation of computing device 210 (e.g., computing device 210 may store data accessed by modules 216, 218, 224, 226, and/or 228 during execution at computing device 210). In some examples, storage component 248 is a temporary memory, meaning that a primary purpose of storage component 248 is not long-term storage. Storage components 248 on computing device 220 may be configured for short-term storage of information as volatile memory and therefore not retain stored contents if powered off. Examples of volatile memories include random access memories (RAM), dynamic random access memories (DRAM), static random access memories (SRAM), and other forms of volatile memories known in the art.

Storage components 248, in some examples, also include one or more computer-readable storage media. Storage components 248 may be configured to store larger amounts of information than volatile memory. Storage components 248 may further be configured for long-term storage of information as non-volatile memory space and retain information after power on/off cycles. Examples of non-volatile memories include magnetic hard discs, optical discs, floppy discs, flash memories, or forms of electrically programmable memories (EPROM) or electrically erasable and programmable (EEPROM) memories. Storage components 248 may store program instructions and/or information (e.g., data) associated with modules 216, 218, 224, 226, and/or 228, as well as data stores 280.

Application modules 224 represent all the various individual applications and services executing at computing device 210. A user of computing device 210 may interact with an interface (e.g., a graphical user interface) associated with one or more application modules 224 to cause computing device 210 to perform a function. Numerous examples of application modules 224 may exist and include, a fitness application, a calendar application, a personal assistant or prediction engine, a search application, a map or navigation application, a transportation service application (e.g., a bus or train tracking application), a social media application, a game application, an e-mail application, a messaging application, an Internet browser application, or any and all other applications that may execute at computing device 210. Although shown separately from application modules 224, activity detection module 216 and/or activity recognition module 218 may be included within one or more of application modules 224 (e.g., included within a fitness application).

As shown in FIG. 2, computing device 210 may include sensor processing modules 226. In some examples, sensor processing modules 226 may receive outputs from sensor components 214 and generate raw sensor component data that represents the outputs. For instance, each of sensor components 214 may have a corresponding sensor processing module. As an example, a sensor processing module for location sensor component 214A may generate GPS coordinate values in raw sensor component data (e.g., objects), where the GPS coordinates are based on hardware outputs of location sensor component 214A. As another example, a sensor processing module for movement sensor component 214C may generate motion and/or acceleration values along different axes of a coordinate system in raw sensor component data, where the motion and/or acceleration values are based on hardware outputs of movement sensor component 214C. Activity recognition module 218 and/or activity detection module 216 may receive the raw sensor component data and further process the data. For instance, activity recognition module 218 may receive raw sensor component data from sensor processing modules 226 and generate ARRs based on the raw sensor component data. Activity detection module 216 may receive raw sensor component data from sensor processing modules 226 to improve the accuracy of detecting the activity in which the user is engaged.

In FIG. 2, activity detection module 216 may detect, based at least in part on sampling a first set of a plurality of sensor components 214 at a first rate, an indication that the user of computing device 210 has initiated a fitness activity, wherein computing device 210 stores pre-defined identifiers of non-fitness and fitness activities in a set of pre-defined indications of activities. Responsive to detecting the indication that the user has initiated the fitness activity, computing device 210 may sample, in an upsampling operational state, at a second rate that is greater than the first rate, a second set of the plurality of sensor components 214 to determine a probability that the user is engaged in the fitness activity, wherein the second set of the plurality of sensor components includes different sensor components than the first set of the plurality of sensors. Responsive to determining that the probability satisfies a threshold, activity detection module 216 and/or one or more of application modules 224 may collect, in an active operational state that is different than the upsampling operational state, sensor data for the fitness activity using a particular set of the plurality of sensor components 214 that corresponds to a pre-defined identifier for the fitness activity in the set pre-defined indications of activities.

As described in FIG. 1, in addition to receiving and/or sampling ARRs at a higher rate in the Upsampling State, activity detection module 216 may receive raw sensor component data to further improve the detection and identification of a particular fitness activity. For instance, activity detection module 216 may receive raw sensor component data from sensor processing modules 226. As an example, activity detection module 216 may receive GPS coordinates and/or a speed from a sensor processing module 226 for location sensor component 214A and may receive a set of motion and/or acceleration values indicating motions and/or accelerations along different axes of a coordinate system (e.g., x, y, and z). Activity detection module 216 may use the raw sensor component data to improve the accuracy of activity detection performed by activity detection module 216. For instance, if activity detection module 216 determines, using HMM or other suitable techniques, that a most probable activity is ON_BICYCLE, but the detected speed is 75 miles per hour, then activity detection module 216 may determine that the user is engaged in the IN_VEHICLE activity instead. That is, if activity detection module 216 detects an anomaly for a fitness activity based on the raw sensor component data, activity detection module 216 may determine the activity engaged in by the user based at least in part on the anomaly. In some examples, activity detection module 216 may apply HMM or other suitable techniques as well to the raw sensor component data to determine a set of probabilities for respective activities. In some examples, the set of probabilities for respective activities based on the raw sensor component data may be combined or otherwise used with the probabilities for the respective activities that are based on applying HMM transformations or other suitable techniques to the ARRs.

In some examples, activity detection module 216 may maintain one or more statistics for how often and/or how much upsampling has been performed by sensor components 214. For instance, activity detection module 216 may maintain or store one or more statistics over a defined period of time, such as hourly, daily, or weekly. In some examples, the statistic may be the total time activity detection module spends in the Upsampling State. In some examples, activity detection module 216 may maintain or store one or more statistics for each sensor component. For instance, activity detection module 216 may store the total amount of time a particular sensor component has been upsampling at the upsampling rate. Activity detection module 216 may store the total amount of batter power consumed by a particular sensor component. The total amount of battery power consumed by a particular sensor component may be the total amount of battery consumption while the sensor component is operating in the Upsampling State.

In some examples, if activity detection module 216 determines that the total amount of batter power consumption for a particular sensor over a defined period of time exceeds a threshold, then activity detection module 216 may not activate the particular sensor component when transitioning from the Normal State to the Upsampling State. In some examples, if the total amount of time that a particular sensor component has been operating in the upsampling state exceeds a threshold, then activity detection module 216 may not activate the particular sensor component when transitioning from the Normal State to the Upsampling State. In some examples, the threshold may represent power consumption or time quotas. As such, activity detection module 216 may enforce power consumption and/or time quotas on a per defined-time period basis (e.g., per day). Once the quota for a particular sensor component is reached, the sensor component will not be upsampled at the upsampling rate for the remainder of the defined time period.

In some examples, activity detection module 216, when operating in the Active State, may use a backoff technique to improve power consumption by reducing the sampling rate of one or more particular sensor components. For instance, a particular activity may be associated with a set of particular sensor components by activity detection module 216. As described in FIG. 1, while operating initially in the Active State, activity detection module 216 may sample an "active state set" of sensor components at an "active sampling" rate. In some examples, activity detection module 216 may decrease the active sampling rate for a particular sensor of the active state set of sensor components over time. For instance, activity detection module 216 may decrease the active sampling rate in a linear, geometric, exponential or other rate of change. Activity detection module 216 may decrease the active sampling rate if the raw sensor component data does not change over a defined period of time (e.g., location is not changing while in Active State because user is running on a treadmill). For example, a user may participate in a 5 hour bike ride. Continuously recording GPS location in the Active State for the user during the 5 hour ride may be battery intensive and drain the battery. Accordingly, activity detection module 216 may initiate higher frequency sampling for the first one hour, followed by a lower frequency sampling for each subsequent hour of the bicycle ride. In this way, activity detection module 216 may provide smoother degradation of the data metrics for the longer-term activities.

As described in FIG. 1, in some examples, computing device 210 may receive information from wearable computing device 100, such as ARRs, raw sensor component data, and any other information that may be created or modified by wearable computing device 100. In some examples, activity detection module 216 may send one or more instructions to wearable computing device 100 that cause wearable computing device 100 to perform functions described with respect to activity detection module 116 and 216. For instance, activity detection module 216 may send one or more instructions to wearable computing device 100 that cause wearable computing device to operate in and/or transition between a Normal State, Upsampling State, and Active State, as described in this disclosure. For example, activity detection module 216 may send one or more instructions to wearable computing device 100 that cause wearable computing device 100 to operate in the same operating state as computing device 210. As such, if activity detection module 216 causes a transition from one state to another, activity detection module 216 may send one or more instructions that cause wearable computing device 100 to perform the same state transition.

In some examples, if activity detection module 216 determines that each of wearable computing device 100 and computing device 210 include the same specific type of sensor component, activity detection module 216 may cause a sensor component of the specific type to sample at only one of either wearable computing device 100 or computing device 210. Activity detection module 216 may, as another example, cause wearable computing device 100 to apply a backoff technique to improve power consumption at wearable computing device 100 by reducing the sampling rate of one or more particular sensor components of wearable computing device 100.

Figure 3:
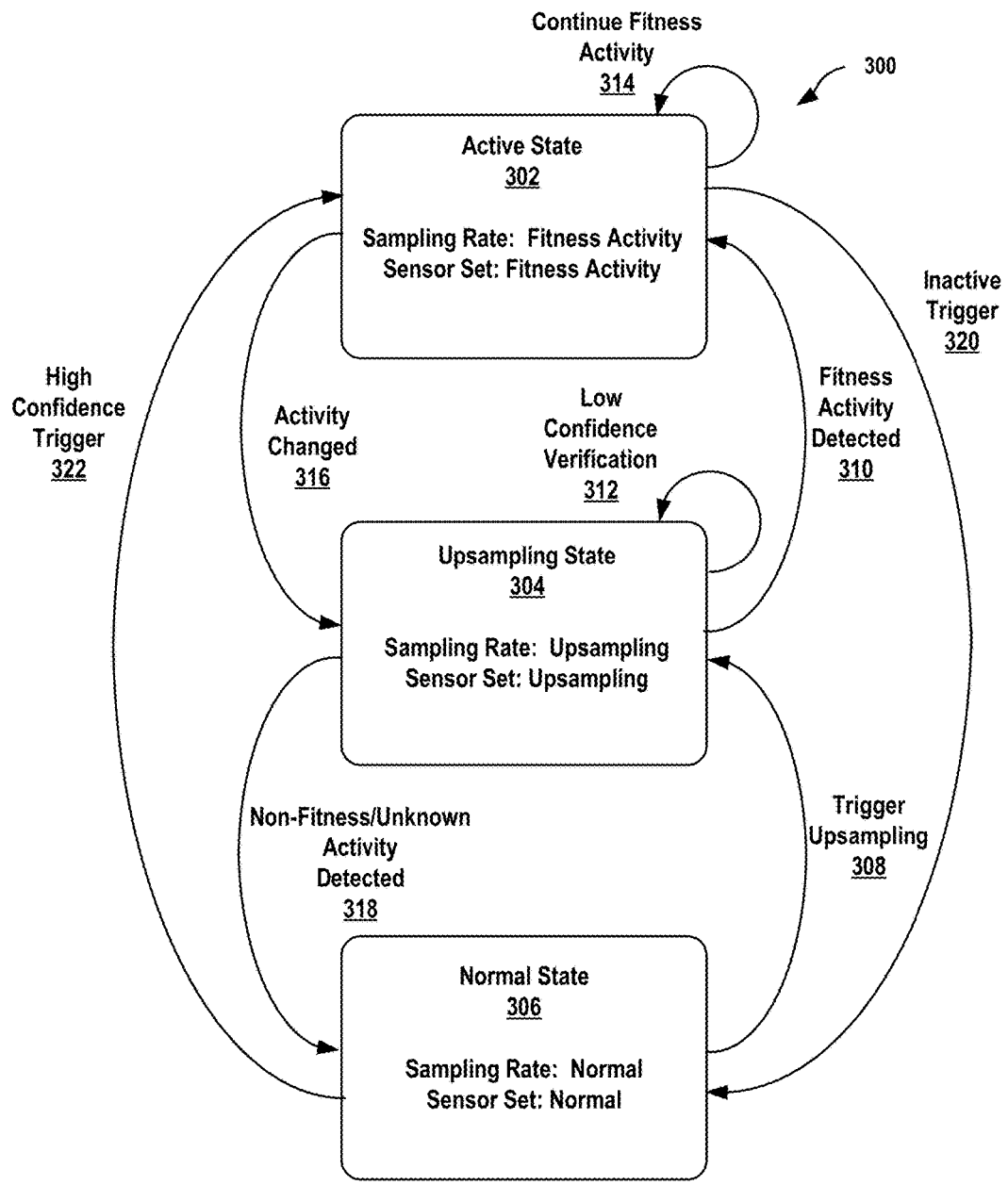
FIG. 3 illustrates an example state machine that may be implemented at a computing device to detect a fitness activity with lower latency and/or greater accuracy by upsampling one or more sensors, in accordance with one or more aspects of the present disclosure.

FIG. 3 illustrates an example state machine 300 that may be implemented at a computing device to detect a fitness activity with lower latency and/or greater accuracy by upsampling one or more sensors, in accordance with one or more aspects of the present disclosure. In some examples, state machine 300 may be implemented in an activity detection module, such as activity detection module 116 and/or 216 as illustrated in FIGS. 1-2. State machine 300 may be implemented as a combination of software and/or hardware in a computing device, such as computing device 110 or 210 and/or wearable computing device 100. For example purposes in FIG. 3, state machine 300 may be implemented in activity detection module 116 of computing device 110, as previously described in FIG. 1.

In the example of FIG. 3, activity detection module 116 may initially operate in the Normal State 306 of state machine 300. For instance, the user may be standing still. Activity detection module 116 may receive ARRs from activity recognition module 118 at a "normal rate" of 1 ARR per minute. As described in FIG. 1, the normal rate may be a pre-defined rate that is set by a user, hard-coded into activity detection module 116, or dynamically updated. While activity detection module 116 operates in the Normal State, activity detection module 116 may perform an HMM transformation on the most recent 30 ARRs that were received once per minute over a 30 minute interval. As described in FIG. 1, in the Normal State, activity recognition module 118 may generate ARRs based on a "normal state set" of sensor components 122, rather than all of the sensors components available to activity recognition module 118.

Activity detection module 116 may later determine that the user has transitioned from a non-fitness activity to a fitness activity. As an example, activity detection module 116 may determine, based at least in part on sampling the normal state set of sensor components at the normal rate, an indication that the user has transitioned from a non-fitness activity to a fitness activity. For example, activity detection module 116 may determine, based on an HMM transformation or other suitable technique, that the user has potentially changed from an activity in the Normal State (e.g., a non-fitness activity) to a fitness activity, such as bicycling. For instance, the highest probability activity from the HMM transformation change from standing still to bicycling. Activity detection module 116 may detect this change from a non-fitness to a fitness activity, which may trigger a state transition 308 to Upsampling State 304.

In Upsampling State 304, activity detection module 116 may cause computing device 110 to sample an "upsampling state set" of sensor components at a "sensor upsampling" rate. The upsampling state set of sensor components may include a greater or different number of sensor components than the normal state set of sensor components as specified by the Normal State. In FIG. 3, while operating in the upsampling state 304, activity detection module 116 may sample five ARRs in a 30 second interval. Each of the ARRs may be generated based on the larger upsampling state set of sensors components, such that the ARRs may more accurately indicate the activity presently engaged in by the user.

In some examples, activity detection module 116 may operate in Upsampling State 304 for a defined period of time, as described in FIG. 1. While operating in the Upsampling State 304, activity detection module 116 may use at least the ARRs generated by activity recognition module 118 during Upsampling State 304 to determine which activity the user is engaged in over a recent period of time. In FIG. 3, activity detection module 116 may run a HMM transformation on two or more of the ARRs generated by activity recognition module 118 while operating in Upsampling State 304. For instance, the HMM transformation may indicate one or more probabilities for one or more respective activities, where each respective probability indicates a likelihood of a user performing the activity.

In Upsampling State 304, activity detection module 116 may determine whether a probability for a fitness activity satisfies a threshold. If none of the respective probabilities for the respective activities satisfies a threshold within a defined period of time, activity detection module 116 may remain in the Upsampling State for an additional defined period of time. That is, none of the respective probabilities for the respective activities satisfies a threshold within a defined period of time, activity detection module 116 may trigger a state transition 312 back to Upsampling State 304. For instance, if none of the respective probabilities for the respective activities satisfies a threshold within a defined period of time, activity detection module 116 may have a low confidence of the actual activity, and therefore continue operating in Upsampling State 304 to determine the actual activity engaged in by the user. In some examples, activity detection module 116 may perform a defined number of state transitions 312 (in some examples, a defined number of consecutive state transitions), and if none of the respective probabilities for the respective activities satisfies a threshold, then activity detection module 116 may transition back to Normal State 306.

In some examples, while in Upsampling State 304, activity detection module 116 may determine, using HMM transformations or other suitable techniques, that the user is engaged in a non-fitness activity. For instance, in Upsampling State 304, activity detection module 116 may determine that the highest probability activity is a non-fitness activity. Accordingly, activity detection module 116 may perform a state transition 318 in which activity detection module 116 transitions from Upsampling State 304 back to Normal State 306 based on detecting the non-fitness activity.

In some examples, while in Upsampling State 304, activity detection module 116 may determine, using HMM transformations or other suitable techniques, that the user is engaged in an unknown activity. For instance, in Upsampling State 304, activity detection module 116 may determine that the highest probability activity is the UNKNOWN activity from the set of pre-defined identifiers. In such examples, activity detection module 116 may perform a state transition 318 to Normal State 306. Activity detection module 116 may also "blacklist" the activity previously detected by activity detection module 116 while operating in Normal State 306 prior to state transition 308. That is, if activity detection module 116 detected a fitness activity RUNNING, which caused state transition 308, and activity detection module determined the highest probability activity in Upsampling State 304 to be UNKNOWN, then activity detection module 116 may blacklist the RUNNING activity for a defined period of time. Blacklisting a particular activity may cause activity detection module 116 to refrain from transitioning to Upsampling State 304 for a defined period of time, although activity detection module 116 otherwise detects the particular activity. In this way, if activity detection module 116 repeatedly detects a particular activity in Normal State 306 that is determined to be UNKNOWN in Upsampling State 304, then activity detection module 116 may refrain from entering the Upsampling State 304 to avoid unnecessarily consuming additional power to determine that the activity is UNKNOWN. After the defined period of time (e.g., the activity is no longer blacklisted), if activity detection module 116 detects the particular activity in Normal State 306 that was previously determined to be UNKNOWN in Upsampling State 304, then activity detection module 116 may again perform state transition 308 to Upsampling State 304.

In some examples, activity detection module 116 may progressively increase the defined period of time for blacklisting an activity, as the activity is consecutively detected without detecting a different activity. For instance, if the same blacklisted activity is detected by activity detection module 116 multiple, consecutive times, activity detection module may increase the defined period of time by a particular amount of time. For instance, each time the same blacklisted activity is consecutively detected, activity detection module 116 may increase the defined period of time by 5 additional minutes for blacklisting.

In some examples, while operating in Upsampling State 304, activity detection module 116 may determine that a probability for a fitness activity satisfies a threshold. As such, activity detection module 116 may determine that it is likely that the user is engaged in the particular fitness activity. Activity detection module 116 may perform a transition 310 from Upsampling State 304 to a different Active State 302. In Active State 302, activity detection module 116 may sample an active state set of sensor components at an active sampling rate. The active state set of sensor components may include a different number of sensor components than the normal state set and/or upsampling state set of sensor components. For instance, in Active State 302, computing device 110 may collect GPS and heartrate data. In Active State 302, computing device 110 may determine change in location as well as distance traveled. The active sampling rate when collecting data from one or more sensor components may be a rate that is different than the normal and/or sensor upsampling rates specified by Normal State 306 and Upsampling State 304.

Activity detection module 116, when transitioning from the Upsampling State to Active State 302, may store, send, or otherwise use an identifier of the fitness activity to select the set of sensors for a particular fitness activity. Activity detection module 116 may use the identifier of the fitness activity to collect data from a set of sensors that are tailored to or are otherwise specific or relevant to the detected fitness activity.

Activity detection module 116 may remain in Active State 302 until activity detection module 116 determines that a change in activity has occurred. For instance, activity detection module 116, while in Active State 302, may continue to receive ARRs from activity recognition module 118. If activity detection module 116 determines, based on one or more ARRs, that the fitness activity remains the same, then activity detection module 116 may perform a state transition 314 to stay in active state 302. That is, activity detection module 116 may remain in Active State 302 and not transition to a state different than Active State 302. If activity detection module 116 determines, based on one or more ARRs, that the fitness activity has changed, then activity detection module 116 may perform a state transition 316 to Upsampling State 304. That is, activity detection module 116 may remain begin operating in Upsampling State 304.

In some examples, while operating in Active State 302, activity detection module 116 may determine, based on one or more ARRs processed by activity detection module 116 in Active State 302, that the user has been inactive for a defined period of time. For instance, activity detection module 116 may have been operating in Active State 302 because the user was engaged in a fitness activity, such as bicycling. However, activity detection module 116 may have later detected that the user is inactive, e.g., the user is no longer engaged in an activity. As an example, the user may have dismounted from the bicycle and set computing device 110 on a stationary surface such as a table. Rather than transitioning back to upsampling state 304, activity detection module 116 may perform a state transition 320 back to normal state 306. In this way, activity detection module 116 may save power that would otherwise have been unnecessarily consumed in Upsampling State 304 because computing device 110 is on the stationary surface (e.g., there is no activity to detect because computing device 110 determines the user to be inactive).

In some examples, while activity detection module 116 operates in the Normal State, activity detection module 116 may perform an HMM transformation ARRs. As described in FIG. 1, in the Normal State, activity recognition module 118 may generate ARRs based on a "normal state set" of sensor components 122, rather than all of the sensors components available to activity recognition module 118. Activity detection module 116 may store at least a high confidence threshold and a moderate confidence threshold, where the high confidence threshold is greater than the moderate confidence threshold. If activity detection module 116 determines, based on the HMM transformations or other suitable techniques, that a fitness activity has a probability greater than the high confidence threshold, then activity detection module 116 may perform a state transition 322 directly to active state 302. As such, activity detection module 116 may bypass Upsampling State 304, which may save power. Activity detection module 116, when transitioning from Normal State 306 directly to Active State 302, may store, send, or otherwise use an identifier of the fitness activity. Activity detection module 116 may use the identifier of the fitness activity, in Active State 302, to collect data from a set of sensors that are tailored to or are otherwise specific or relevant to the detected fitness activity.

Figure 4:
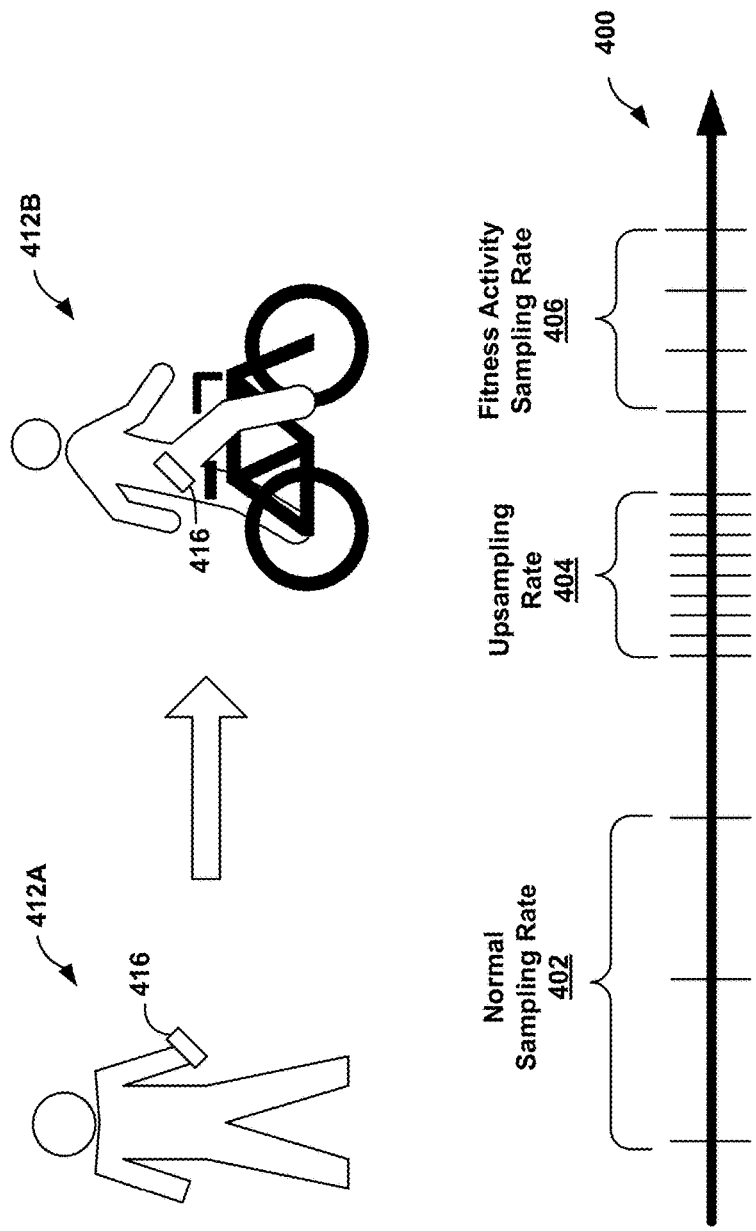
FIG. 4 includes an example timeline that illustrates sampling rates for detecting a fitness activity with lower latency and/or greater accuracy by upsampling one or more sensors, in accordance with one or more aspects of the present disclosure.

FIG. 4 includes an example timeline 400 that illustrates sampling rates for detecting a fitness activity with lower latency and/or greater accuracy by upsampling one or more sensors, in accordance with one or more aspects of the present disclosure. For example purposes in FIG. 4, timeline 400 is described in the context of an activity detection module of computing device 416, which may be an example of computing device 110 or 210 as described in FIGS. 1-2. In the example of FIG. 4, the activity detection module may initially operate in a Normal State. For instance, the user may be standing still. The activity detection module may receive ARRs from an activity recognition module at a "normal rate" 402 of 1 ARR per minute.

While the activity detection module operates in the Normal State, the activity detection module may perform an HMM transformation on a most recent n-number of ARRs that were received once per minute. The activity detection module of computing device 416 may detect that the user is engaged in an activity STILL 412A because the user remains still. The STILL activity may have a pre-defined identifier in the activity detection module. The activity detection module may later determine that the user has transitioned from a non-fitness activity 412A to a fitness activity 412B, such as ON_BICYCLE. For example, the activity detection module may determine, based on an HMM transformation or other suitable technique, that the user has potentially changed from an activity STILL 412A in the Normal State (e.g., a non-fitness activity) to a fitness activity 412B ON_BICYCLE.

In the Upsampling State, the activity detection module may cause computing device 416 to sample an "upsampling state set" of sensor components at a "sensor upsampling" rate 404. In FIG. 4, while operating in the Upsampling State, the activity detection module may sample an ARR every three seconds for a one minute interval. Each of the ARRs may be generated based on the larger upsampling state set of sensors components, such that the ARRs may more accurately indicate the activity presently engaged in by the user.

In the Upsampling State, the activity detection module may determine whether a probability for a fitness activity satisfies a threshold. In some examples, the activity detection module may operate at the upsampling rate 404 for a defined period of time, and if none of a set of respective probabilities for the respective activities satisfies a threshold, the activity detection module may transition back to the Normal State. In some examples, if the activity detection module determines that the user is engaged in a non-fitness activity, the activity detection module may transition back to the Normal State.

In some examples, while operating in the Upsampling State, the activity detection module may determine that a probability for fitness activity 412B satisfies a threshold. The activity detection module may determine that it is likely that the user is engaged in the particular fitness activity 412B. In the Active State, the activity detection module may sample an active state set of sensor components at an active sampling rate 406. For instance, the active sampling rate 406 may be one sample every 30 seconds while in the Active State. The active state set of sensor components may include a different number of sensor components than the normal state set and/or upsampling state set of sensor components. The active sampling rate 406, when collecting data from one or more sensor components, may be a rate that is different than the normal sampling rate 402 and/or the sensor upsampling rate 404 specified by the Normal State and the Upsampling State.

Figure 5:
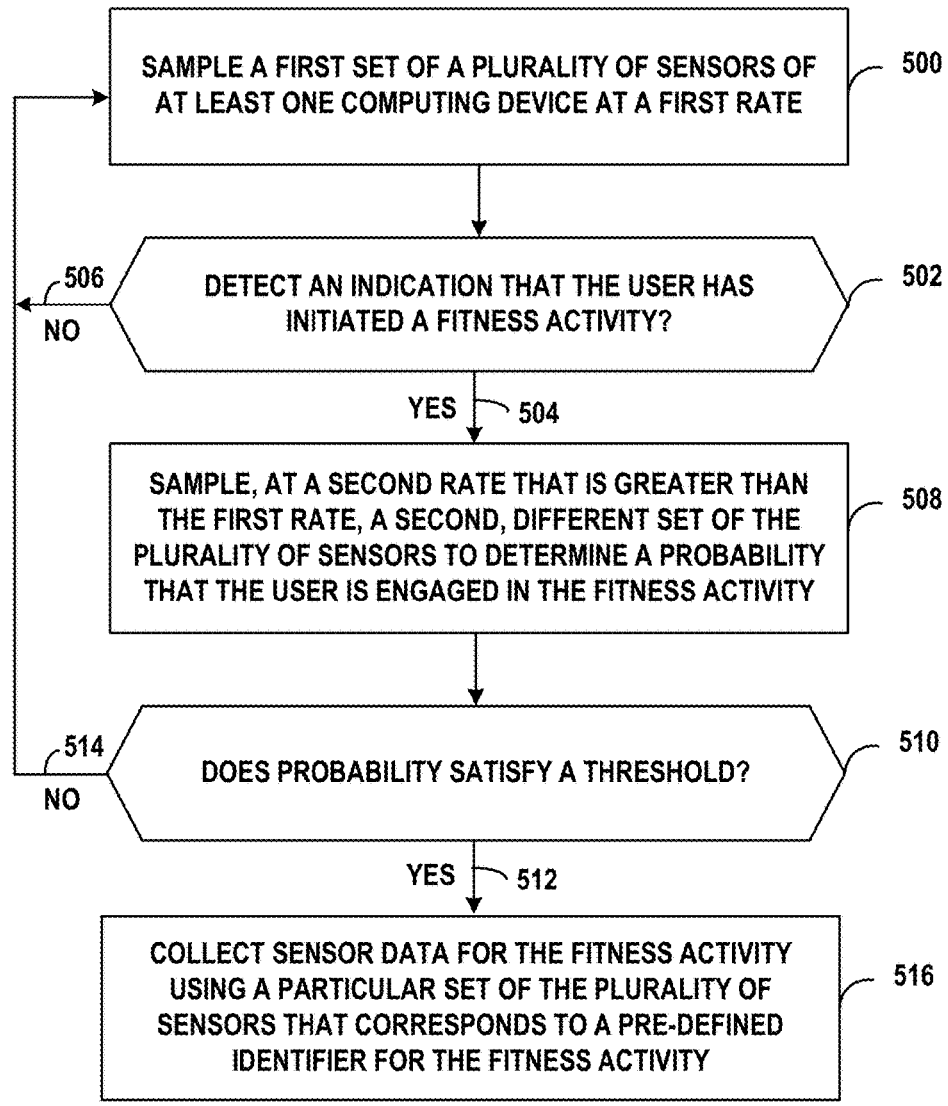
FIG. 5 is a flow diagram illustrating example operations of a computing device that may detect a fitness activity with lower latency and/or greater accuracy by upsampling one or more sensors, in accordance with one or more aspects of the present disclosure.

FIG. 5 is a flow diagram illustrating example operations of a computing device that may detect a fitness activity with lower latency and/or greater accuracy by upsampling one or more sensors, in accordance with one or more aspects of the present disclosure. For purposes of illustration only, the example operations are described below within the context of computing device 110 of FIG. 1. In some examples, activity detection module 116 may perform the techniques of FIG. 5.

In FIG. 5, computing device 110 may initially operate in the Normal State. Computing device 110 may sample (500) ARRs at a "normal rate." For example, computing device 110 may sample a first set of sensors of at the normal rate. In the Normal State, computing device 110 may generate and/or receive ARRs based on a "normal state set" of sensor components, rather than all of the sensors components included in and/or available to computing device 110. For instance, a normal state set of sensor components may include an accelerometer sensor component, but may exclude other sensor components available to computing device 110.

While computing device 110 operates in the Normal State, computing device 110 may perform HMM transformations or other suitable techniques on the one or more ARRs to detect the activity engaged in by the user. In the Normal State, computing device 110 may generate ARRs based on the "normal state set" of sensor components. Based on applying one or more techniques to a defined quantity of ARRs, computing device 110 may determine (502) whether the user has transitioned from a non-fitness activity to a fitness activity. As an example, computing device 110 may detect an indication that the user has initiated a fitness activity. In some examples, computing device 110 may not detect, based at least in part on sampling the normal state set of sensor components at the normal rate, an indication that the user has transitioned from a non-fitness activity to a fitness activity (506). Accordingly, computing device 110 may continue sampling at the normal rate with the normal state set of sensor components.

In some examples, computing device 110 may detect, based at least in part on sampling the normal state set of sensor components at the normal rate, an indication that the user has transitioned from a non-fitness activity to a fitness activity (504). Computing device 110, in response to determining the indication that the user has changed from non-fitness activity to fitness activity, may transition from the Normal State to the Upsampling State. In the Upsampling State, computing device 110 may sample (508) an "upsampling state set" of sensor components at a "sensor upsampling" rate. The upsampling state set of sensor components may include a greater number of sensor components than the normal state set of sensor components as specified by the Normal State. In some examples, the upsampling state set of sensor components may include different subset of all sensor components available to and/or included in computing device 110 than the normal state set of sensor components.

As described in FIG. 1, while operating in the Upsampling State, computing device 110 may use at least the ARRs generated during the Upsampling State to determine which activity the user is engaged in over a recent period of time. In some examples, one or more HMM transformations performed on the ARRs may indicate one or more probabilities for one or more respective activities, where each respective probability indicates a likelihood of a user performing the activity. Activity detection module 116 may determine whether a probability for a fitness activity satisfies a threshold (e.g., a probability is greater than, greater than or equal to, less than, less than or equal to, or equal to the threshold) (510). In some examples, if none of the respective probabilities for the respective probabilities satisfies a threshold (514), then computing device 110 may revert operation back to the Normal State of operation (500).

In some examples, while operating in the Upsampling State, computing device 110 may determine that a probability for a fitness activity satisfies a threshold (512). As such, computing device 110 may determine that it is likely that the user is engaged in the particular fitness activity. Computing device 110 may transition to an Active State that is different than the Upsampling State. In the Active State, computing device may sample an "active state set" of sensor components at an "active sampling" rate. The active state set of sensor components may include a different number of sensor components than the normal state set and/or upsampling state set of sensor components.

Computing device 110 may collect (516) data from a set of sensors that are tailored to or are otherwise specific or relevant to the detected fitness activity. In some examples, the active sampling rate when collecting data from one or more of sensors components, may be a rate that is different than the normal and/or sensor upsampling rates specified by the Normal State and Upsampling States, respectively. For instance, the active sampling rate may be a rate that is greater than or less than the normal and/or sensor upsampling rates specified by the Normal State and Upsampling States.

In some examples, techniques of the disclosure implementing sensor upsampling may reduce false positives and/or allows a computing device to resolve a user's activity with higher accuracy and lower latency. The additional sensor data may also consumed by the underlying activity recognition module, which may help improve the activity recognition accuracy as well. A high accuracy and low latency activity detection module may improve a computing device's collection of fitness information for activities like running or biking, without requiring a user to explicitly instruct an the computing device that the user has started/stopped a fitness activity.

Example 1

A method comprising detecting, by a computing device of a user and based at least in part on sampling a first set of a plurality of sensors of the computing device at a first rate, an indication that the user has initiated a fitness activity, wherein the computing device stores pre-defined identifiers of non-fitness and fitness activities in a set of pre-defined indications of activities; responsive to detecting the indication that the user has initiated the fitness activity, sampling, by the computing device in an upsampling operational state, at a second rate that is greater than the first rate, a second set of the plurality of sensors to determine a probability that the user is engaged in the fitness activity, wherein the second set of the plurality of sensors includes different sensors than the first set of the plurality of sensors; and responsive to determining that the probability satisfies a threshold, collecting, by the computing device in an active operational state that is different than the upsampling operational state, sensor data for the fitness activity using a particular set of the plurality of sensors that corresponds to a pre-defined identifier for the fitness activity in the set of pre-defined indications of activities.

Example 2

The method of Example 1, wherein the computing device detects the indication that the user has initiated the fitness activity in a normal operational state, wherein the method further comprises: determining, by the computing device, the pre-defined identifier for the fitness activity; and determining, by the computing device, the threshold based at least in part on the pre-defined identifier for the fitness activity.

Example 3

The method of any of Examples 1-2, wherein the computing device consumes more power when operating in the upsampling operational state than in either of the normal operational state or the active operational state.

Example 4

The method of any of Examples 1-3, further comprising: determining, by the computing device while operating in a normal operational state, the pre-defined identifier for the fitness activity; and determining, by the computing device and based at least in part on the pre-defined identifier for the fitness activity, at least one of the second rate for the upsampling operational state or the second set of the plurality of sensors for the upsampling operational state.

Example 5

The method of any of Examples 1-4, further comprising: determining, by the computing device while operating in a normal operational state, the pre-defined identifier for the fitness activity; and determining, by the computing device and based at least in part on the pre-defined identifier for the fitness activity, at least one of a third rate of sampling the particular set of the plurality of sensors for the active operational state or the particular set of the plurality of sensors for the active operational state.

Example 6

The method of any of Examples 1-5, further comprising: determining, by the computing device while operating in the active operational state, that values generated by at least one sensor of the particular set of the plurality of sensors that corresponds to the pre-defined identifier have not changed for a defined period of time; and decreasing, by the computing device and in response to determining that the values have not changed for the defined period of time, a third rate of sampling the at least one sensor.

Example 7

The method of any of Examples 1-6, wherein the fitness activity is a first fitness activity, further comprising: generating, by the computing device while operating in the upsampling operational state, activity recognition results (ARRs) based at least in part on raw sensor component data from the second set of the plurality of sensors, wherein at least one of the ARRs indicates the probability for the first fitness activity; detecting, by the computing device and in the raw sensor component data, an anomaly for a second fitness activity; and selecting, by the computing device, based at least in part on the at least one of the ARRs and the anomaly in the raw sensor component data, the first fitness activity, wherein a probability of the second fitness activity is greater than the probability for the first fitness activity.

Example 8

The method of any of Examples 1-7, further comprising: prior to detecting the indication that the user has initiated the fitness activity, determining, by the computing device, a first pre-defined identifier of an activity engaged in by the user while the computing device is operating in the normal operational state; responsive to detecting the indication that the user has initiated the fitness activity, determining, by the computing device while operating in the upsampling operational state, that an unknown activity is associated with a highest probability in a set of probabilities associated with the set pre-defined indications of activities; blacklisting, by the computing device and for a pre-defined period of time, the first pre-defined identifier of the activity; and responsive to detecting a second pre-defined identifier of an activity engaged in by the user in the normal operational state, refraining, while the pre-defined identifier of the activity is blacklisted, from operating in the upsampling operational state, wherein the first and second pre-defined identifiers are the same.

Example 9

The method of any of Examples 1-8, further comprising, increasing the pre-defined period of time for each consecutive determination by the computing device that the unknown activity is associated with the highest probability in the set of probabilities associated with the set pre-defined indications of activities.

Example 10

The method of any of Examples 1-9, further comprising: storing, by the computing device, a battery usage statistic that indicates an amount of power consumed, during the upsampling operational state, by at least one sensor of the plurality of sensors; and responsive to determining that the at least one battery usage statistic satisfies a threshold, refraining, by the computing device, from sampling the at least one sensor at the second rate in response to detecting the indication that the user has initiated the fitness activity.

Example 11

The method of any of Examples 1-10, where the threshold is a first threshold and the probability is a first probability, the method further comprising: responsive to detecting, while operating in the normal operational state, that a second probability of the fitness activity is greater than a second threshold, changing operation of the computing device directly to the active operational state from the normal operational state without transitioning to the upsampling operational state, wherein the second threshold is greater than the first threshold.

Example 12

The method of any of Examples 1-11, further comprising: responsive to detecting, while in the active operational state, that the user has changed from the fitness activity to a different activity, changing operation of the computing device from the active operational state to the upsampling operational state.

Example 13

The method of any of Examples 1-12, further comprising: responsive to detecting the indication that the user has initiated the fitness activity, sending, by the computing device and to a wearable computing device, one or more instructions that cause the wearable computing device to sample a third set of sensors of the wearable computing device at the second rate; and receiving, by the computing device and from the wearable computing device, information from the wearable computing device that is based at least in part on raw sensor component data generated by the wearable computing device at the second rate.

Example 14

The method of any of Examples 1-13, further comprising: responsive to determining that the wearable computing device includes at least one sensor of the same type as at least one sensor of the second set of the plurality of sensors, sending, by the computing device and to the wearable computing device, one or more instructions that cause the wearable computing device to refrain from sampling the at least one sensor of the wearable computing device at the second rate.

Example 15

The method of any of Examples 1-14, wherein the indication that the user has initiated the fitness activity is based at least in part on receiving information from a wearable computing device, wherein the information from the wearable computing device is based at least in part on raw sensor component data generated by the wearable computing device.

Example 16

A non-transitory computer-readable storage medium encoded with instructions that, when executed, cause at least one processor of a computing device for a user to: detect, based at least in part on sampling a first set of a plurality of sensors of the computing device at a first rate, an indication that the user has initiated a fitness activity, wherein the computing device stores pre-defined identifiers of non-fitness and fitness activities in a set of pre-defined indications of activities; responsive to detecting the indication that the user has initiated the fitness activity, sample, in an upsampling operational state, at a second rate that is greater than the first rate, a second set of the plurality of sensors to determine a probability that the user is engaged in the fitness activity, wherein the second set of the plurality of sensors includes different sensors than the first set of the plurality of sensors; and responsive to determining that the probability satisfies a threshold, collect, in an active operational state that is different than the upsampling operational state, sensor data for the fitness activity using a particular set of the plurality of sensors that corresponds to a pre-defined identifier for the fitness activity in the set pre-defined indications of activities.

Example 17

The non-transitory computer-readable storage medium of Example 16 encoded with instructions that, when executed, cause at least one processor of the computing device to: determine, while operating in a normal operational state, the pre-defined identifier for the fitness activity; and determine, based at least in part on the pre-defined identifier for the fitness activity, at least one of the second rate for the upsampling operational state or the second set of the plurality of sensors for the upsampling operational state.

Example 18

The non-transitory computer-readable storage medium of any of Examples 16 or 17, wherein the computing device consumes more power when operating in the upsampling operational state than in either of the normal operational state or the active operational state.

Example 19

A non-transitory computer-readable storage medium encoded with instructions that, when executed, cause at least one processor of a computing device for a user to perform any of Examples 2-15.

Example 20

A computing device comprising: one or more computer processors; a plurality of sensors operably coupled to the one or more computer processors; and a memory comprising instructions that when executed by the one or more computer processors cause the one or more computer processors to: detect, based at least in part on sampling a first set of the plurality of sensors of the computing device at a first rate, an indication that a user of the computing device has initiated a fitness activity, wherein the computing device stores pre-defined identifiers of non-fitness and fitness activities in a set of pre-defined indications of activities; responsive to detecting the indication that the user has initiated the fitness activity, sample, by the computing device in an upsampling operational state, at a second rate that is greater than the first rate, a second set of the plurality of sensors to determine a probability that the user is engaged in the fitness activity, wherein the second set of the plurality of sensors includes different sensors than the first set of the plurality of sensors; and responsive to determining that the probability satisfies a threshold, collect, by the computing device in an active operational state that is different than the upsampling operational state, sensor data for the fitness activity using a particular set of the plurality of sensors that corresponds to a pre-defined identifier for the fitness activity in the set of pre-defined indications of activities.

Example 21

The computing device of Example 20, wherein the memory comprises instructions that when executed by the one or more computer processors cause the one or more computer processors to: determine, while operating in a normal operational state, the pre-defined identifier for the fitness activity; and determine, based at least in part on the pre-defined identifier for the fitness activity, at least one of the second rate for the upsampling operational state or the second set of the plurality of sensors for the upsampling operational state.

Example 22

A computing device comprising: one or more computer processors; a plurality of sensors operably coupled to the one or more computer processors; and a memory comprising instructions that when executed by the one or more computer processors cause the one or more computer processors to perform any of the methods of Examples 2-15.

Example 23

An apparatus comprising: means for detecting, based at least in part on sampling a first set of a plurality of sensors of the computing device at a first rate, an indication that a user of the apparatus has initiated a fitness activity, wherein the apparatus stores pre-defined identifiers of non-fitness and fitness activities in a set of pre-defined indications of activities; responsive to detecting the indication that the user has initiated the fitness activity, sampling, by the apparatus in an upsampling operational state, at a second rate that is greater than the first rate, a second set of the plurality of sensors to determine a probability that the user is engaged in the fitness activity, wherein the second set of the plurality of sensors includes different sensors than the first set of the plurality of sensors; and responsive to determining that the probability satisfies a threshold, collecting, by the apparatus in an active operational state that is different than the upsampling operational state, sensor data for the fitness activity using a particular set of the plurality of sensors that corresponds to a pre-defined identifier for the fitness activity in the set pre-defined indications of activities.

Example 24

The apparatus of example 21 comprising means for performing any of the methods of Examples 2-15.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the embodiment, certain acts or events of any of the methods described herein can be performed in a different sequence, may be added, merged, or left out all together (e.g., not all described acts or events are necessary for the practice of the method). Moreover, in certain embodiments, acts or events may be performed concurrently, e.g., through multi-threaded processing, interrupt processing, or multiple processors, rather than sequentially.

In some examples, a computer-readable storage medium includes a non-transitory medium. In some examples, the term "non-transitory" indicates that the storage medium is not embodied in a carrier wave or a propagated signal. In certain examples, a non-transitory storage medium may store data that can, over time, change (e.g., in RAM or cache). Although certain examples are described as outputting various information for display, techniques of the disclosure may output such information in other forms, such as audio, holographical, or haptic forms, to name only a few examples, in accordance with techniques of the disclosure.

Various examples have been described. These and other examples are within the scope of the following claims.

What is claimed is:

1. A method for conserving power while reducing latency in collecting sufficient information for identifying particular fitness activities being performed by users of computing devices, the method comprising:
 determining, by a computing device while operating in a normal operational state of the computing device and based at least in part on applying a first Hidden Markov Model transformation to a sampling of a first set of a plurality of sensors of the computing device taken at a first rate that is a slowest rate from among three sampling rates so as to conserve power, whether a user of the computing device has transitioned from performing a non-fitness activity to initiating any fitness activity, wherein:
  the computing device stores pre-defined identifiers of non-fitness and fitness activities in a set of pre-defined indications of activities;
  determining whether the user of the computing device has transitioned from performing the non-fitness activity to initiating any fitness activity comprises identifying initial data from the first Hidden Markov Model transformation that precedes subsequent data from the first Hidden Markov Model transformation;

the initial data corresponds to one or more of the pre-defined identifiers of non-fitness activities in the set of predefined indications of activities; and the subsequent data corresponds to one or more of the pre-defined identifiers of fitness activities in the set of predefined indications of activities;

responsive to determining that the user has transitioned from performing the non-fitness activity to initiating any fitness activity and until a probability that the user is engaged in a particular fitness activity satisfies a threshold, sampling, by the computing device while operating in an upsampling operational state of the computing device that uses more power than the normal operational state of the computing device, at a second rate that is a fastest rate from among the three sampling rates so as to more quickly obtain sufficient sensor data for identifying the particular fitness activities, a second set of the plurality of sensors to collect the sufficient sensor data to determine the probability that the user is engaged in a particular fitness activity, wherein the second set of the plurality of sensors includes a greater quantity of sensors than the first set of the plurality of sensors, wherein the probability that the user is engaged in the particular fitness activity is determined in part by applying a second Hidden Markov Model transformation to the sufficient sensor data;

responsive to determining that the probability satisfies the threshold, collecting, by the computing device in an active operational state of the computing device that uses less power than the upsampling operational state and more power than the normal operating state, at a third rate that is greater than the first rate and less than the second rate so as to efficiently collect fitness information, additional sensor data as fitness information associated with the particular fitness activity, the additional sensor data being collected from a particular set of the plurality of sensors that corresponds to a pre-defined identifier for the particular fitness activity in the set of pre-defined indications of activities; and outputting, via a user interface of the computing device, the fitness information associated with the particular activity that was collected during the active operational state.

2. The method of claim 1, wherein the method further comprises:
determining, by the computing device, the pre-defined identifier for the particular fitness activity; and
determining, by the computing device, the threshold based at least in part on the pre-defined identifier for the particular fitness activity.

3. The method of claim 1, further comprising:
determining, by the computing device while operating in the normal operational state, the pre-defined identifier for the particular fitness activity; and
determining, by the computing device and based at least in part on the pre-defined identifier for the particular fitness activity, at least one of the second rate for the upsampling operational state or the second set of the plurality of sensors for the upsampling operational state.

4. The method of claim 1, further comprising:
determining, by the computing device while operating in the normal operational state, the pre-defined identifier for the particular fitness activity; and
determining, by the computing device and based at least in part on the pre-defined identifier for the particular fitness activity, at least one of the third rate of sampling the particular set of the plurality of sensors for the active operational state or the particular set of the plurality of sensors for the active operational state.

5. The method of claim 1, further comprising:
determining, by the computing device while operating in the active operational state, whether values, generated by at least one sensor of the particular set of the plurality of sensors that corresponds to the pre-defined identifier, have changed for a defined period of time; and
decreasing, by the computing device and in response to determining that the values have not changed for the defined period of time, the third rate of sampling the at least one sensor.

6. The method of claim 1, wherein the particular fitness activity is a first fitness activity, the method further comprising:
generating, by the computing device while operating in the upsampling operational state, activity recognition results (ARRs) based at least in part on raw sensor component data from the second set of the plurality of sensors, wherein at least one of the ARRs indicates the probability for the first fitness activity;
detecting, by the computing device, an anomaly in the raw sensor component data for a second fitness activity; and
selecting, by the computing device, based at least in part on the at least one of the ARRs and the anomaly in the raw sensor component data, the first fitness activity, wherein a probability of the second fitness activity is greater than the probability for the first fitness activity.

7. The method of claim 1, further comprising:
prior to determining that the user has transitioned from performing the non-fitness activity to initiating any fitness activity, determining, by the computing device, a first pre-defined identifier of an activity engaged in by the user while the computing device is operating in the normal operational state;
further responsive determining that the user has transitioned from performing the non-fitness activity to initiating any fitness activity, determining, by the computing device while operating in the upsampling operational state, that an unknown activity is associated with a highest probability in a set of probabilities associated with the set pre-defined indications of activities;
blacklisting, by the computing device and for a pre-defined period of time, the first pre-defined identifier of the activity; and
responsive to detecting a second pre-defined identifier of an activity engaged in by the user while the computing device is operating in the normal operational state, refraining, while the pre-defined identifier of the activity is blacklisted, from operating in the upsampling operational state, wherein the first and second pre-defined identifiers are the same.

8. The method of claim 7, further comprising, increasing the pre-defined period of time for each consecutive determination by the computing device that the unknown activity is associated with the highest probability in the set of probabilities associated with the set pre-defined indications of activities.

9. The method of claim 1, further comprising:
storing, by the computing device, a battery usage statistic that indicates an amount of power consumed, during the upsampling operational state, by at least one sensor of the plurality of sensors; and responsive to determining that the at least one battery usage statistic satisfies a threshold, refraining, by the computing device, from sampling the at least one sensor at the second rate in response to determining that the user has transitioned from performing the non-fitness activity to initiating any fitness activity.

10. The method of claim 1, where the threshold is a first threshold and the probability is a first probability, the method further comprising:
responsive to detecting, while operating in the normal operational state, that a second probability of the particular fitness activity is greater than a second threshold, changing operation of the computing device directly to the active operational state from the normal operational state without transitioning to the upsampling operational state, wherein the second threshold is greater than the first threshold.

11. The method of claim 1, further comprising:
responsive to detecting, while in the active operational state, that the user has changed from the particular fitness activity to a different activity, changing operation of the computing device from the active operational state to the upsampling operational state.

12. The method of claim 1, further comprising:
responsive to determining that the user has transitioned from performing the non-fitness activity to initiating any fitness activity, sending, by the computing device and to a wearable computing device, one or more instructions that cause the wearable computing device to sample a third set of sensors of the wearable computing device at the second rate; and
receiving, by the computing device and from the wearable computing device, information from the wearable computing device that is based at least in part on raw sensor component data generated by the wearable computing device at the second rate.

13. The method of claim 12, further comprising:
responsive to determining that the wearable computing device includes at least one sensor of the same type as at least one sensor of the second set of the plurality of sensors, sending, by the computing device and to the wearable computing device, one or more instructions that cause the wearable computing device to refrain from sampling the at least one sensor of the wearable computing device at the second rate.

14. The method of claim 1, wherein determining whether the user of the computing device has transitioned from performing the non-fitness activity to initiating any fitness activity is based at least in part on receiving information from a wearable computing device, wherein the information from the wearable computing device is based at least in part on raw sensor component data generated by the wearable computing device.

15. The method of claim 1, wherein the non-fitness activity comprises at least one of sitting or standing.

16. The method of claim 1, wherein the non-fitness activity comprises walking.

17. A non-transitory computer-readable storage medium encoded with instructions that, when executed, cause at least one processor to:
determine, while a computing device is operating in a normal operational state of the computing device and based at least in part on applying a first Hidden Markov Model transformation to a sampling of a first set of a plurality of sensors of the computing device taken at a first rate that is a slowest rate from among three sampling rates so as to conserve power, whether a user of the computing device has transitioned from performing a non-fitness activity to initiating any fitness activity, wherein:
the computing device stores pre-defined identifiers of non-fitness and fitness activities in a set of pre-defined indications of activities;
the at least one processor determines whether the user of the computing device has transitioned from performing the non-fitness activity to initiating any fitness activity comprises identifying initial data from the first Hidden Markov Model transformation that precedes subsequent data from the first Hidden Markov Model transformation;
the initial data corresponds to one or more of the pre-defined identifiers of non-fitness activities in the set of predefined indications of activities; and
the subsequent data corresponds to one or more of the pre-defined identifiers of fitness activities in the set of predefined indications of activities;
responsive to determining that the user has transitioned from performing the non-fitness activity to initiating any fitness activity and until a probability that the user is engaged in a particular fitness activity satisfies a threshold, sample, while the computing device is operating in an upsampling operational state of the computing device that uses more power than the normal operational state of the computing device, at a second rate that is a fastest rate from among the three sampling rates so as to more quickly obtain sufficient sensor data for identifying particular fitness activities, a second set of the plurality of sensors collect the sufficient sensor data to determine the probability that the user is engaged in a particular fitness activity, wherein the second set of the plurality of sensors includes a greater quantity of sensors than the first set of the plurality of sensors, wherein the probability that the user is engaged in the particular fitness activity is determined in part by applying a second Hidden Markov Model transformation to the sufficient sensor data;
responsive to determining that the probability satisfies the threshold, collect, while the computing device is operating in an active operational state of the computing device that uses less power than the upsampling operational state and more power than the normal operating state, at a third rate that is greater than the first rate and less than the second rate so as to efficiently collect fitness information, additional sensor data as fitness information associated with the particular fitness activity, the additional sensor data being collected from a particular set of the plurality of sensors that corresponds to a pre-defined identifier for the fitness activity in the set of pre-defined indications of activities; and
output, via a user interface of the computing device, the fitness information associated with the particular activity that was collected during the active operational state.

18. The non-transitory computer-readable storage medium of claim 17 encoded with instructions that, when executed, cause the at least one processor to:
determine, while the computing device is operating in the normal operational state, the pre-defined identifier for the particular fitness activity; and
determine, based at least in part on the pre-defined identifier for the particular fitness activity, at least one of the second rate for the upsampling operational state or the second set of the plurality of sensors for the upsampling operational state.

19. A computing device comprising:
one or more computer processors;
a plurality of sensors operably coupled to the one or more computer processors; and
a memory comprising instructions that when executed by the one or more computer processors cause the one or more computer processors to:
determine, while the computing device is operating in a normal operational state of the computing device and based at least in part on applying a first Hidden Markov Model transformation to a sampling of a first set of a plurality of sensors of the computing device taken at a first rate that is a slowest rate from among three sampling rates so as to conserve power, whether a user of the computing device has transitioned from performing a non-fitness activity to initiating any fitness activity, wherein:
the computing device stores pre-defined identifiers of non-fitness and fitness activities in a set of pre-defined indications of activities;
the one or more processors determine whether the user of the computing device has transitioned from performing the non-fitness activity to initiating any fitness activity comprises identifying initial data from the first Hidden Markov Model transformation that precedes subsequent data from the first Hidden Markov Model transformation;
the initial data corresponds to one or more of the pre-defined identifiers of non-fitness activities in the set of predefined indications of activities; and
the subsequent data corresponds to one or more of the pre-defined identifiers of fitness activities in the set of predefined indications of activities;
responsive to determining that the user has transitioned from performing the non-fitness activity to initiating any fitness activity and until a probability that the user is engaged in a particular fitness activity satisfies a threshold, sample, while the computing device is operating in an upsampling operational state of the computing device that uses more power than the normal operational state of the computing device, at a second rate that is a fastest rate from among the three sampling rates so as to more quickly obtain sufficient sensor data for identifying particular fitness activities, a second set of the plurality of sensors collect the sufficient sensor data to determine the probability that the user is engaged in a particular fitness activity, wherein the second set of the plurality of sensors includes a greater quantity of sensors than the first set of the plurality of sensors, wherein the probability that the user is engaged in the particular fitness activity is determined in part by applying a second Hidden Markov Model transformation to the sufficient sensor data;
responsive to determining that the probability satisfies the threshold, collect, while the computing device is operating in an active operational state of the computing device that uses less power than the upsampling operational state and more power than the normal operating state, at a third rate that is greater than the first rate and less than the second rate so as to efficiently collect fitness information, additional sensor data as fitness information associated with the particular fitness activity, the additional sensor data being collected from a particular set of the plurality of sensors that corresponds to a pre-defined identifier for the fitness activity in the set of pre-defined indications of activities; and
output, via a user interface of the computing device, the fitness information associated with the particular activity that was collected during the active operational state.

20. The computing device of claim 19, wherein the memory comprises instructions that when executed by the one or more computer processors cause the one or more computer processors to:
determine, while the computing device is operating in the normal operational state, the pre-defined identifier for the particular fitness activity; and
determine, based at least in part on the pre-defined identifier for the particular fitness activity, at least one of the second rate for the upsampling operational state or the second set of the plurality of sensors for the upsampling operational state.

* * * * *